(12) United States Patent　　　　(10) Patent No.:　US 12,616,483 B2

Mayer et al.　　　　　　　　　　　(45) Date of Patent:　　　May 5, 2026

(54) DEVICE AND METHOD FOR PERFORATING A DENSE BONE LAYER

(71) Applicant: BOSONIC AG, Bern (CH)

(72) Inventors: Jörg Mayer, Niederlenz (CH); Andrè Schwery, Biberist (CH); Loïc Sottas, Lausanne (CH); Dominique Neuhaus, Zürich (CH)

(73) Assignee: BOSONIC AG, Bern (CH)

( * ) Notice: Subject to any disclaimer, the term of this patent is extended or adjusted under 35 U.S.C. 154(b) by 967 days.

(21) Appl. No.: 17/278,442

(22) PCT Filed: Sep. 24, 2019

(86) PCT No.: PCT/EP2019/075759
§ 371 (c)(1),
(2) Date: Mar. 22, 2021

(87) PCT Pub. No.: WO2020/064768
PCT Pub. Date: Apr. 2, 2020

(65) Prior Publication Data
US 2021/0353306 A1　　Nov. 18, 2021

(30) Foreign Application Priority Data

| Sep. 24, 2018 | (CH) | ..................................... | 01166/18 |
| Nov. 29, 2018 | (CH) | ..................................... | 01472/18 |
| Mar. 8, 2019 | (CH) | ..................................... | 00282/19 |

(51) Int. Cl.
　　*A61B 17/32*　　　(2006.01)
　　*A61B 17/16*　　　(2006.01)
　　　　　　　　(Continued)

(52) U.S. Cl.
　　CPC .. *A61B 17/1659* (2013.01); *A61B 17/320068* (2013.01); *B33Y 80/00* (2014.12);
　　　　　　　　(Continued)

(58) Field of Classification Search
　　CPC ........... A61B 2017/00473; A61B 2017/00526; A61B 2017/320073; A61B 2017/320074; B33Y 80/00
　　See application file for complete search history.

(56) References Cited

U.S. PATENT DOCUMENTS

| 5,261,922 A | 11/1993 | Hood | |
| 5,318,570 A * | 6/1994 | Hood ................. | A61B 17/8847 601/2 |

(Continued)

FOREIGN PATENT DOCUMENTS

| CN | 105310746 | 2/2016 |
| JP | 2015-536760 A | 12/2015 |

(Continued)

*Primary Examiner* — Elizabeth Houston
*Assistant Examiner* — Jonathan A Hollm
(74) *Attorney, Agent, or Firm* — Rankin, Hill & Clark LLP

(57) ABSTRACT

A device for cutting bone tissue and, more particularly, a sonotrode suitable for use with an ultrasonic surgical instrument. The sonotrode has a head and a distal end piece, the distal end piece being equipped as a rectangular blade for cutting bones using mechanical vibration. The sonotrode has at least one structural element and the structural element is selected from the group including: a support structure, a lateral depression on each side, an increased width of the blade together with a slit at the distal end of the blade, or at least one lateral rib.

30 Claims, 20 Drawing Sheets

(51) Int. Cl.
  *B33Y 80/00*          (2015.01)
  *A61B 17/00*              (2006.01)
(52) U.S. Cl.
  CPC .............. *A61B 2017/00473* (2013.01); *A61B 2017/00526* (2013.01); *A61B 2017/320073* (2017.08); *A61B 2017/320074* (2017.08)

(56)                    References Cited

U.S. PATENT DOCUMENTS

| | | | | |
|---|---|---|---|---|
| 9,622,767 | B2 * | 4/2017 | Stoddard | ........ A61B 17/320092 |
| 2006/0253050 | A1 * | 11/2006 | Yoshimine | ......... A61H 23/0245 |
| | | | | 601/2 |
| 2007/0123893 | A1 * | 5/2007 | O' Donoghue | ...... A61B 17/142 |
| | | | | 606/82 |
| 2008/0300591 | A1 * | 12/2008 | Darian | ........... A61B 17/320068 |
| | | | | 606/41 |

| | | | | |
|---|---|---|---|---|
| 2012/0004729 | A1 | 1/2012 | Zipnick | |
| 2013/0096596 | A1 | 4/2013 | Schafer | |
| 2013/0204285 | A1 * | 8/2013 | Gouery | .......... A61B 17/320068 |
| | | | | 606/169 |
| 2014/0163595 | A1 | 6/2014 | Witt et al. | |
| 2015/0005771 | A1 | 1/2015 | Voic | |
| 2015/0007704 | A1 | 1/2015 | Vieira | |
| 2016/0128769 | A1 | 5/2016 | Rontal et al. | |
| 2017/0340339 | A1 * | 11/2017 | Madan | ........... A61B 17/320068 |
| 2018/0014844 | A1 | 1/2018 | Conlon | |

FOREIGN PATENT DOCUMENTS

| | | |
|---|---|---|
| WO | 2013/057179 | 4/2013 |
| WO | 2017/150444 | 9/2017 |
| WO | 2018/040918 | 3/2018 |
| WO | 2018/153248 | 8/2018 |

* cited by examiner 4     12     11     5     6

3     2     1

4 5 6 14

4 5 6 19 14

4 12 5 14

4     5     6     10  9     14

13   4     12     11          15          7

13     4     12     11     15   7   9   14

13   12   7   26   46   15   25   9   14.1   14.2

13   12   7   26   25   9   14

13   12   20   20

13   4   12   20

13    4  12    15 18  7                                              20

13      4  12        18  7    20              7      18

13              4      12      11        15      7

4 38.1 37 38.2 38.3 38.4 38.5 6 9

12 37 38

A A 4 39 12 5 6 9

A-A 4 40 41 39 9

A-A

DEVICE AND METHOD FOR PERFORATING A DENSE BONE LAYER

BACKGROUND OF THE INVENTION

Field of the Invention

The invention resides in the field of medical technology and concerns a device for cutting bone tissue. It relates in particular to a sonotrode suitable to be used with an ultrasonic surgical instrument.

Description of Related Art

Among the cutting devices for cutting bone tissue, ultrasonic instruments are particularly efficient. These instruments include a cutting head that for the process is pressed against the bone tissue and is set into ultrasonic oscillation. The cutting process by these instruments is basically based on a local smashing of bone tissue. Transport of debris away from the cutting location as well as cooling are major issues.

Cutting devices for cutting bone tissue, for example in osteotomy processes, on the one hand need to be equipped to cut through very dense and strong cortical bone tissue, and this at different angles (because of different access situations). On the other hand, cutting devices need to be capable of cutting deep into for example cancellous bone tissue.

Prior art instruments include instruments with a cranked cutting device. The advantage using said instruments is a high amplitude in transverse direction. The main disadvantage of said instruments is their high pressure sensitivity: such cranked cutting devices are not sufficiently stiff in working (forward) direction.

WO 2013/057179 discloses a sonotrode for a surgical instrument. The sonotrode head serves as cutting device extending in a longitudinal direction. It has a plurality of perforations extending in transverse direction through the sonotrode head. The perforations have an oblong shape and are at an angle between 30° and 80° to the longitudinal direction, whereby the sonotrode head gains an elasticity and, when subject to the ultrasonic vibrations, makes a pitching motion in the plane defined by the sonotrode head. According to WO 2013/057179, nevertheless a sufficient stiffness for applying a pressing force is preserved. The cutting surface of the sonotrode head further includes indentations that assist a removal of dissolved bone material.

US 2015/0005771 A1 describes sonotrodes having a planar blade body, wherein the blade body has two lateral sides and a shallow recess. These sonotrodes have a shank with an outlet communicating with the recess, thereby enabling liquid flow into the recess. The blade further has a through hole extending between the lateral surfaces of the blade body and enabling liquid flow from the recess to an opposing side of the blade. US 2012004729 A1 describes cutting instruments with a longitudinal blade having a cutting edge build by a rim around an opening extending through the blade. The cutting takes place by rotation not by oscillation.

The ultrasonic surgical instrument BoneScapel® has a rather thick sonotrode of more than 1 mm thickness with a circumferentially flattened tip or distal end of the blade. Thus, it includes a thick sonotrode with sharpened edges to cut the bone.

SUMMARY OF THE INVENTION

It is an object of the present invention to provide an improved sonotrode for an ultrasonic surgical instrument suitable for cutting bones using mechanical vibration as well as an ultrasonic surgical instrument for cutting bones, including an improved sonotrode and methods for manufacturing these sonotrodes. One goal to be achieved by the improved sonotrodes is a better cutting performance for cortical bone. Cortical bone is dense and compact. Thereby the reduction of heat produced during cutting of bones is envisaged. In addition, it would be favorable to be able to lengthen the cutting surface of the sonotrode in order to allow deeper bone cuts such as osteotomy. One problem for long sonotrodes are bending movements such as oscillations out of plane, which have to be avoided. At the same time a thicker blade of the sonotrode should be avoided. Therefore, the blade does not need a sharpened distal end as cutting edge.

Therefore, the present invention refers to a sonotrode for an ultrasonic surgical instrument having a head and a distal end piece, the distal end piece being equipped as a rectangular blade for cutting bones using mechanical vibration, wherein the sonotrode includes at least one structural element and wherein said element is selected from the group comprising: a support structure, a lateral depression on each side, an increased width of the blade together with a slit at the distal end of the blade, or at least one lateral rib.

A first aspect of the invention relates to a sonotrode for an ultrasonic surgical instrument having a head and a distal end piece, the distal end piece being equipped as a blade for cutting bones using mechanical vibration, wherein the blade has a lateral depression on each side. The blade may be mainly rectangular. Nevertheless, the distal end of the blade may be arcuate or the blade may have rounded ends.

The term "proximal" as used herein refers to the nearest to the point of attachment to the housing of an ultrasonic surgical instrument or respectively to the user of that instrument. The term "distal" as used herein refers to being situated away from the point of attachment to the housing of an ultrasonic surgical instrument or respectively to the user of that instrument. Thus, the distal end and the proximal end are opposite ends.

An alternative formulation of the above embodiment is the following: a sonotrode for an ultrasonic surgical instrument having a head and a distal end piece, the distal end piece being equipped as a blade for cutting bones using mechanical vibration, wherein the blade has a central area of reduced thickness. The depression or central area of reduced thickness may by rectangular. It is preferred that the depression or central area of reduced thickness has rounded corners or a semicircular distal and/or proximal end. The depression or central area of reduced thickness may encompass 50-90% of the surface of the blade. Thus, the inventive sonotrode may include a blade having a rim surrounding the depression or central area of reduced thickness. The width of said rim may be 0.3 to 1.5 mm. The rim may be uniform. In other words the dimensions of the rim may be consistent around the depression. In another embodiment the rim is thicker at the proximal end of the depression than at the distal end. The depression may have a v-shaped proximal part pointing towards the head of the sonotrode.

Another embodiment of the invention refers to a sonotrode for an ultrasonic surgical instrument having a head and a distal end piece, the distal end piece being equipped as a blade for cutting bones using mechanical vibration, wherein the blade has a lateral depression on each side and wherein the lateral depression has two different levels. In other words the depression includes at least two areas with different depths. The depression may have a proximal area and a distal area, wherein the proximal area has a reduced depth compared to the distal area. The distal area may be formed to have a peak at its proximal end pointing to the head of the sonotrode.

The blade may have a substantially rectangular shape with a first edge being a cutting edge and a second edge, being an edge opposite the first edge. In a planar alignment with a flat surface of said blade is a central region wherein a depression s arranged. It is thereby preferred that the cutting edge is not sharpened. This means, the distal end of the blade is preferably not flattened. The blade or the rim around the depression may have a constant or unvaried thickness.

One embodiment of the first aspect of the invention refers to a sonotrode wherein the lateral depressions have the same depth and are symmetrically arranged within the blade. It is preferred that the blade of the sonotrode as well as the sonotrode is symmetrically build. The blade is most preferably symmetric to its longitudinal middle axis. This axis runs from the proximal end of the head until the distal end of the blade.

Another embodiment of the first aspect of the invention refers to a sonotrode, wherein the lateral depressions have each a depth of 0.2 to 0.5 mm and preferably of around 0.1 mm. This means the blade has a central area where the thickness is reduced. It is preferably reduced about 0.5 to 1.0 mm and more preferred the thickness is reduced about 0.2 mm. Another embodiment of the first aspect of the invention refers to a sonotrode, wherein the blade of the sonotrode has a rim surrounding the depression or the central area of reduced thickness and further has a groove running parallel to that rim. In other words the depression or the central area of reduced thickness of the sonotrode blade is bound by a rim and a groove inside that rim. The groove defines a level being lower than the level of the rim and the depression. It is preferred that the depression has no sharp edges and that the transition of the rim to the depression or the groove is smooth. Therefore, it is preferred that the transition between the rim and the surface of the groove or respectively the depression is continuously or in form of a curvature. In case that the transition is curved, it is possible to create a defined but stable cutting edge. The form of a curvature can be shaped like the letter S or being sigmoid.

Furthermore, the area of reduced thickness of a sonotrode according to the first aspect may have an elevated structure. This structure can include ribs running parallel to each other and preferably parallel to the longitudinal axis of the sonotrode blade. The ribs may also be arranged to form a grid or regular mesh. It is preferred that the cross section of the elevated structure and in particular of the at least one rib is selected in a way that the structure (or rib) does not protrude above the rim of the blade surrounding the depression. The ribs increase the stiffness of the blade and respectively the sonotrode. Nevertheless, the friction is lowered and the cooling capacity is still improved. Alternatively to ribs, the elevated structure may also be formed by cubes, cuboids, frustums of pyramid, cylinders (right circular cylinder, oblique circular cylinder) or of n-gonal prisms where n is between 3 and 16.

In order to reduce the torsion of the sonotrode the elevated structure in form of ribs may be oblique to the longitudinal axis of the blade. It is preferred that the ribs form an angle with the longitudinal axis of the sonotrode or the blade of 30 to 60°. These ribs being oblique may be crossed and thus forms a grid. The distance between the ribs may be between 0.2 and 0.7 mm. The distance between the elevated structure may also be formed by cubes, cuboids, frustums of pyramid, cylinders (right circular cylinder, oblique circular cylinder) or of n-gonal prisms where n is between 3 and 16 may be between 0.2 and 1.0 mm. The height of the elevated structures is preferably between 0.1 and 0.5 mm.

Another embodiment of the first aspect of the invention refers to a sonotrode, wherein the blade of the sonotrode has channels running from the area of the depression to the edge of the blade. In other words, there are channels or grooves running from the area of reduced thickness to the edge of the blade. The channels or grooves may have the same depth as the depression. It is preferred that the channels or grooves are present on each lateral side of the blade. The channels may be at corresponding position on each side or are staggered. It is preferred that the channels or grooves are open towards the surface of the blade. Therefore, they can have a semicircular or edged shape. The channels or grooves may be arranged towards the cutting edge only. They may also run towards the distal end. There may also be embodiments wherein the channels and grooves are arranged symmetrically around the depression or area of reduced thickness. There may be between 5 to 10 channels or grooves per lateral side of the blade.

Despite the reduced thickness in a large area of the blade the sonotrode is stable enough to cut also cortical bones without destroying the sonotrode. In addition, the performance of the sonotrode is not reduced by side bending or torsion modes.

It could be observed that the sonotrode having depressions within their blade has the following advantages compared to sonotrodes according to prior art. The heat produced during bone cutting is clearly reduced. This may be caused due to a reduction of the friction between the flat sides of the blade and the bone, thus minimizing energy impact. Another mechanism could be that a cooling liquid commonly used during bone cutting, can build a constant film on the surface of the blade. Furthermore, the depressions and in particular the channels or grooves on the lateral surface of the blade assist in transport o bone debris out of the bone cut. The advantage of less temperature increase is in particular helpful for deep cuts, where efficient cooling is a big problem. In addition, the reduced friction involves less power loss, especially if the surgeon does not perfectly guide the cutting edge in the axis. Furthermore, the risk that the sonotrode blade gets stuck in the bone because of tilting or getting jammed is reduced as the area with full thickness is reduced.

The sonotrodes according to the present invention may include a cooling system. The cooling system may have at least one exit port of each side of the sonotrode, preferably symmetrically arranged. The exit port can be arranged at the head of the sonotrode and in particular within the flattening area of the head. The exit port may be located in a way that the central longitudinal axis of the sonotrode (A-A) runs through the exit port. The cooling system may further be designed to have at least one central channel for liquid supply. This central channel may run along the central axis through the housing or hand piece of the sonotrode up to or into the head of the sonotrode. Within the head of the sonotrode the central channel may split into two feeding channels ending with the exit port. The feeding channels may be arranged symmetrically and in a way that at least the distal end of each feeding channel forms an acute ankle with the longitudinal axis of the sonotrode blade. The cooling system may also include a cavity within the head of the sonotrode or the distal end of the housing. This cavity can serve as a reservoir for the cooling liquid. At the distal end the reservoir may have two discharge openings. These discharge openings can be connected to feeding channels. The liquid may flow through these feeding channels up to the exit ports. The feeding channels have therefore preferably a slope or gradient (compared to the central channel or the longitudinal axis of the sonotrode).

In order to avoid heat damage to the surrounding tissue, it is desirable for the splinters ablated from the bone to be removed from the operating field in a speedy fashion. If the splinters were to remain in the operating field, they would act as a type of heat store and increase the effect of the heat on the surrounding tissue. The removal of splinters or bone debris can be supported by depressions and/or channels as described above. The inventors could observe that the removal of splinters or bone debris can alternatively be promoted by a sonotrode undertaking a nodding motion. The sonotrode then acts in the style of a shovel that removes the debris. Thus, the second aspect of the invention refers to a sonotrode having a design that adds to the dominant x-amplitude of the vibration a significant z-amplitude. This causes further that the bone is not only cut by pushing movements but also by cutting movements. This increases further the cutting performance and allows improved cutting of cortical bones.

It could have been observed that due to minimization of the friction and with an improved control of the cutting direction (minimizing the tendency to get jammed in the incision) it is enough to shift the natural frequencies (fundamental frequency and strong harmonic frequencies) for the vibration modes in bending or torsion of cutting sonotrodes out of the range of the excitation frequency about ±1 kHz to get an optimized thin and precise cut.

It has been shown that a sonotrode with a slit at the distal end of its blade resulting in two prongs oscillating against each other results in the wanted shift of frequencies. One embodiment of the present invention refers to a sonotrode for an ultrasonic surgical instrument having a head and a distal end piece, the distal end piece being equipped as a blade for cutting bones using mechanical vibration, wherein the width of the blade is increasing towards its distal end and the blade has a slit at its distal end.

Thereby it is preferred that the width increases continuously and decreases because of an arcuate distal end of the blade. The increase in the width may only occur in the distal half of the blade or the two distal third of the blade but should not start directly at the head of the sonotrode. The slit should run perpendicular to the plane defined by the flat surface of the blade. It can start from the most distal point of the blade. Thereby the slit may essentially run along the middle axis. Thus, the second aspect of the present invention refers preferably to a sonotrode, wherein the slit runs from the most distal point of the blade edge towards the head of the sonotrode. The length of the slit may be between 2 and 8 mm. The width may be between 0.2 mm and 1 mm. It is preferred that the width increases towards the distal end of the slit and also the blade. The increase may be continuously or starting abruptly at one point within the course of the slit. It is preferred that the sonotrode according to the invention has a slit having a V-shape, a U-shape or a Y-shape.

The design of the sonotrode with the slit at the distal end of the plate allows z-oscillation (upside down movement) in addition to longitudinal (x-) oscillation but without showing y-oscillation. Therefore, the bending resonance has to be far away from longitudinal resonance.

The bone material that has been broken down when using the sonotrode according to the second aspect of the invention can be removed from the work region as a result of a nodding movement intrinsically carried out by the sonotrode while the sonotrode vibrates. Thus, the sonotrode is not prevented from penetrating deeper into the bone material. This is especially helpful for cutting dense bone.

In order to cut very dense and hard bone, such as the cortex, it may be helpful that the blade of the sonotrode includes peaks. Such peaks may enhance the piercing capacity of the sonotrodes according to the invention. The peak should preferably be located in a way that it is the first structure to penetrate the bone. The location is preferably at the distal end of the blade and may vary depending on the design of the distal end piece of the sonotrode and the angle the sonotrode has when it impinges on the surface of the bone.

Therefore, the present invention refers to a sonotrode for an ultrasonic surgical instrument having a head and a distal end piece, the distal end piece being equipped as a blade for cutting bones using mechanical vibration, wherein the blade includes a peak at its distal end. Thereby the peak may be at the corner of the cutting edge located at the distal end of the blade. Such a peak may be formed when the corner has a radius of less than 0.5 mm. Nevertheless, it is preferred that there is a radius, preferably >0.1 mm, thus a rounded corner exists. This reduces the risk of harm to the surrounding soft tissue. Such a peak is also formed when the distal end of the blade has the shape of a dovetail. Therefore, the distal side of the blade may have a concave form (hollowed inwardly). This concave form may be semicircular or nearly semicircular but it may also be parabolic or tapered such as v-shaped.

Alternatively, the peak at the distal end is located on the central, longitudinal axis of the sonotrode. Thus, the present invention refers to a sonotrode for an ultrasonic surgical instrument having a head and a distal end piece, the distal end piece being equipped as a blade for cutting bones using mechanical vibration, wherein the blade includes a peak at its distal end so that the distal end has the form of an arrow head.

The sonotrodes of the present invention may have a waisted blade. Therefore, the present invention refers to a sonotrode for an ultrasonic surgical instrument having a head and a distal end piece, the distal end piece being equipped as a blade for cutting bones using mechanical vibration, wherein blade includes a peak at its distal end and is waisted. In another embodiment the sonotrode blade may have barbs (harp projection extending backward) at the lateral edge(s), such as the cutting edge. It is preferred that these barbs are not provided on the complete length of the edge, but are located only in the distal part, such as the most distal third or quarter. The barbs may be located at a wasted blade optionally including a peak at its distal end. The present invention refers also to a sonotrode for an ultrasonic surgical instrument having a head and a distal end piece, the distal end piece being equipped as a blade for cutting bones using mechanical vibration, wherein blade is waisted and includes a peak at its distal end and barbs at the lateral cutting edge. In combination with the waist, the barbs allow the sonotrode to cut through the bone or the cortex by diving into the bone (resp. the cortex) and remove material on the return movement, so that ablation of bone is possible both in the forward movement using the peak as well as in the backward movement using the barbs. The waist allows both to tilt the blade in the plane and thus to grip deeper under the cortex during retraction and to minimize friction on the edge and thus counteract pinching.

It is also possible that the distal end has a convex form with a peak at the most distal point. Therefore, the present invention refers to a sonotrode for an ultrasonic surgical instrument having a head and a distal end piece, the distal end piece being equipped as a blade for cutting bones using mechanical vibration, wherein blade includes a peak at its distal end being formed like a spearhead or an arrowhead. Alternatively, the peak may be located at the distal end of the slit (at the transition between slit and circumference of the blade) of a sonotrode designed according to the second aspect. The peaks located at the distal end of the slit may be formed to protrude distally of the blade, maybe in form of a sharp tip or a spike.

For cutting deeply into bone the sonotrode should be longer. But as longer as higher is the risk of torsion movement. The inventors found that a sonotrode for an ultrasonic surgical instrument having a head and a distal end piece, the distal end piece being equipped as a blade for cutting bones using mechanical vibration, wherein the sonotrode has at least one rib such as a reinforcing rib, avoids torsional bending with nearly optimal longitudinal frequency of around 27000 Hz.

Therefore, a third aspect of the invention refers to a sonotrode for an ultrasonic surgical instrument having a head and a distal end piece, the distal end piece being equipped as a blade for cutting bones using mechanical vibration, wherein the sonotrode has at least one rib. The at least one rib may also be called a reinforcing or stiffening rib. One embodiment of the third aspect of the present invention refers to a sonotrode, wherein the sonotrode has at least one lateral rib on each side (each flat side). Another embodiment of this aspect refers to a sonotrode, wherein the sonotrode or respectively the blade of the sonotrode has at least two lateral ribs on each side.

The ribs are attached to the lateral or flat side of the sonotrode and/or respectively to the blade having a longitudinal, thin rectangular form. It is preferred that the at least one rib runs along the central axis of the sonotrode. It has been found to be advantageously that the at least one rib runs along the head and the distal end piece. Nevertheless, the at least one rib may run only along distal end piece of the sonotrode.

Another embodiment refers to a sonotrode according to the invention, wherein the at least one rib has a flattened distal end. Also, the proximal end may be flattened. In this case the flattening out at the proximal end may be steeper than at the distal end. The rib on the sonotrode does not have to have the same length than the sonotrode or the blade o the sonotrode. A preferred embodiment of the present invention refers to a sonotrode, wherein the distal end of the at least one rib lies in the middle third of blade length. The rib may have a semicircular or angular cross section. The rib should be continuously. It may have a high and/or a width of 0.05 mm to 0.5 mm. Each rib or fin may be radially upstanding to a constant height above the blade. The ribs allow to shift the natural frequencies (fundamental frequency and strong harmonic frequencies) for the vibration modes in bending or torsion clearly out of the range of the excitation frequency (at least ±1 kHz).

A fourth aspect of the invention relates to a sonotrode for an ultrasonic surgical instrument having a head and a distal end piece, the distal end piece being equipped as a blade for cutting bones using mechanical vibration, wherein the blade is arched or bent. This means the blade is not designed lying in a flat plane. It is preferred that blade of the sonotrode has a cross section shaped as an arc. The cross section formed like an arch is preferably the cross section being perpendicular to the longitudinal axis of the sonotrode. The arch can be a circular arch, a parabolic arch or a catenary arch. A circular arch is preferred. The arched or crescent shape of the blade may be symmetrical to the longitudinal axis defined by the middle axis of the sonotrode head. In addition, the tangent that touches the curve of the blade in the point where the curve cuts the longitudinal middle axis of the sonotrode head built an acute angle of at least 5° with the tangent that touches the curve in the outermost point. A sonotrode according to the fourth aspect of the invention has a cross section in form of a circle segment.

This sonotrode is particular suitable for working axial. It allows to cut or abrade in corners or foramina of bones. One preferred use is cutting osteophytes to get decompression. A sonotrode according to the fourth aspect may have a lateral depression on each lateral side as described for the first aspect of the present invention. All points described before in relation to the depression applies to the embodiments of the fourth aspect, too.

The blade may be mainly rectangular. Nevertheless, the distal end of the blade may be flattened or sharpened. Thus, one embodiment of the fourth aspect of the invention relates to a sonotrode for an ultrasonic surgical instrument having a head and a distal end piece, the distal end piece being equipped as a blade for cutting bones using mechanical vibration, wherein the blade is bent and has a sharpened distal edge as cutting edge. In another embodiment of the sonotrode according to the fourth aspect the corners of the distal edge are not rounded but sharp and serve as cutting edge. Nevertheless, it is also possible that the lateral edge of the blade is used and formed as a cutting edge. With such a blade one can abrade something (such as a bone cyst) or scrape something out.

Furthermore, the sonotrode may have a rib as described for the third aspect of the invention. All points described before in relation to the rib applies to the embodiments of the fourth aspect, too. In addition, the rib may be at a sharpened distal end of the blade. One or more ribs may also be part of the sonotrode having a depression. In this case it is preferred that the cross section of the rib is selected in a way that the rib does not protrude above a rim of the blade surrounding the depression. It is preferred that the rib has no sharp edges and that the transition of the rib to the blade is smooth. Therefore, it is preferred that the transition between the rib and the blade surface is continuously or in form of a curvature.

Beside a rib the sonotrode may also have several spacers aligned along a longitudinal axis of the sonotrode. The spacers can be attached to the blade in a symmetrical pattern. The spacers may also be part of the sonotrode having a depression. In this case it is preferred that the cross section of the spacers is selected in a way that the spacer do not protrude above a rim of the blade surrounding the depression.

A fifth aspect of the invention refers to a sonotrode for an ultrasonic surgical instrument having a head and a distal end piece, the distal end piece being equipped as a blade for cutting bones using mechanical vibration, wherein the blade include at least one step. The blade of the sonotrode may include two steps. Each step is defined as a reduction in thickness of the blade. Thereby, the thickness distal of the step decreases. The reduction of the thickness can occur continuously within an area or suddenly. Each step defines a level proximal of the step and a level distal of the step. The steps have the advantage that the stiffness of the blade is increased but the cutting edge at the distal end is thin. This allows the combination of high stiffness of the blade so that the sonotrode may be longer and allows fine and precise cuts.

Furthermore, the sonotrode may have a rib as described for the third aspect of the invention. All points described before in relation to the rib applies to the embodiments of the fifth aspect, too. It is further preferred that the number and arrangement of the ribs of different levels differ.

The following statements or implementations relates to all aspects described herein.

The sonotrode according to the invention regularly includes a shaft being part of the sonotrode head. A connection to the ultrasound transducer can be established via the other end of the shaft. The shaft is preferably aligned in the longitudinal direction of the blade. The shaft forms the proximal end of the sonotrode head; the distal end is situated opposite thereto. For connection of the sonotrode according to the invention the shaft may include or be built by a thread. Alternative connections are possible too, such as a plug-in or push-in connection, clamping connection, or clip connections. One possibility to adapt the distal end of the head to the proximal end of the blade is to include a flattening area at the distal end of the sonotrode head. Therefore, one embodiment of the invention refers to a sonotrode wherein the head has a thread at its proximal end.

In addition, the head of the sonotrode and the distal end piece respectively the blade are preferably formed together as one piece or may be rigidly attached to each other. Therefore, the distal end of the sonotrode head may have the same cross section as the proximal end of the blade or a cross section adapted to the proximal end of the distal end piece, respectively the blade. The head of the sonotrode according to the present invention is preferably formed as a circular cylinder but the blade is a rather thin part. Therefore, one embodiment of the invention refers to a sonotrode wherein the head has a flattened distal end. Alternatively, the sonotrode head may have a flattened cross section, such as an ellipsoid or oval cross section.

In general, the distal end piece or respectively blade of the sonotrode should be built without any perforation or break-through. Also, the channels, grooves or depressions described above are areas of a reduced thickness but it is preferred that these areas does not include a through-bore. Also, the complete sonotrode blade does preferably not include a through bore.

The extent of the blade in the longitudinal direction can lie between 15 mm and 60 mm, preferably between 18 mm and 30 mm. The extent of the blade in the transverse direction can, for example, be between 1 mm and 20 mm, preferably between 2 mm and 10 mm. The extent in the longitudinal direction is regularly greater than the extent in the transverse direction. The height perpendicular to the longitudinal direction and the transverse direction can likewise lie between 0.3 mm and 1.5 mm (height of the distal end or blade without optional ribs). One embodiment of the invention relates to a sonotrode, wherein the blade of the sonotrode has a length of 15 to 40 mm. Another embodiment of the invention relates to a sonotrode, wherein the blade of the sonotrode has a thickness of 0.3 to 2 mm, preferably 0.4 mm to 1 mm. Another embodiment of the invention relates to a sonotrode, wherein the blade of the sonotrode has a width of 3 to 7.5 mm. The distal end of the sonotrode is preferably rounded. This means that the corners of the rectangular blade are rounded or that the distal end has a semicircular form. The sonotrode according to the invention has a form typical for flat spatulas used in laboratories. Therefore, one embodiment of the invention refers to a sonotrode wherein the blade of the sonotrode has an arcuate distal end portion.

Alternatively, the distal end portion of the blade is not arcuate but is formed to have different facets. Each facet is a small plane surface at the distal edge of the blade. Thus, three or more peaks may result at the distal end, where different facets hit each other. The peaks resulting from the facets may be rounded. This means the facets or planes are interconnected by small arcs.

Also, the lateral edges of the blade may be rounded off. It is preferred that at least the lateral edges and corners are rounded. The lateral edges may be rounded with a radius corresponding to the half of the thickness of the blade. The radius should be not less than one third of the thickness of the blade. The radius of the lateral edges may be between 0.15 mm and 0.4 mm. The radius of the corners may be between 0.15 and 0.6 mm and preferably between 0.2 and 0.5 mm.

In addition, the sonotrodes according to the present invention may include a support structure or stiffening structure. Such a support structure may be attached to the proximal end of the blade. It may also start within the head of the sonotrode, in particular at the flattening area of the sonotrode head. It is preferred that the support structure is symmetrically attached to both lateral sides of the inventive sonotrode. The border may be flattened. Thus, the translation from the support structure to the blade may have the shape of a sigmoid curve or may be shaped as a ramp.

The support structure may be a thickening of the proximal end of the sonotrode, which preferably spans the complete width of the blade. It may have a length between 2 and 6 mm, more preferably between 2.5 and 4.5 mm and the maximal thickness can be between 0.03 and 0.25 mm and preferably between 0.05 and 0.2 mm. The support structures in the form of a thickening may have a length of 15 to 35% (preferably 18-30% and more preferred 20 to 25%) of the maximal length of the blade. The thickness of the support structure is $\frac{1}{20}$ to $\frac{1}{4}$ (preferably $\frac{1}{15}$ to $\frac{1}{5}$) of the thickness of the blade.

The distal end of the support structure may be wave shaped, whereby a wave through is positioned on the central axis of the sonotrode.

Alternatively, the support structure may have the shape of a frame around a circular void space and, in particular, may have the shape of a ring. It is preferred that the support structure being ring shaped includes a central round void space, which may be positioned central on the central axis of the blade. The ring shaped support structure may have maximal thickness between 0.03 and 0.15 mm, preferably between 0.08 and 0.12 mm. The outer radius of the ring may be between 3.5 and 5.5 mm, preferably between 4 and 5 mm and the inner radius may be between 2 and 4 mm or further preferred between 2.5 and 3.5 mm. The ring shaped support structure may be attached symmetrically on both sides of the blade. Thus, in the case that the blade has a thickness of 0.5 mm the thickness with the attached ring shaped support structures, having a thickness of 0.1 mm each, is in total 0.7 mm.

The support structure may have an increasing radius at the most distal point. This means the maximal length or the maximal outer radius is up to half times larger than the minimal outer radius. The support structure can be egg shaped. The ring or egg-shaped support structures may have a diameter respectively maximal diameter of 15 to 35% (preferably 18-30% and more preferred 20 to 25%) of the maximal length of the blade. The thickness of the support structure is $\frac{1}{25}$ to $\frac{1}{5}$ (preferably $\frac{1}{20}$ to $\frac{1}{10}$) of the thickness of the blade.

The ring shaped support structure may further include a cross beam. The cross beam runs preferably along the central longitudinal axis of the blade. The cross beam may have the length of the outer diameter of the ring shaped support structure. In another embodiment the cross beam extends beyond the ring and protrudes towards the distal end of the blade. The maximal length of the cross beam is 16 mm, preferred 14 mm and further preferred 12 mm. The length of the cross beam may be not more than two third of the maximal length of the blade. In addition, the length of the cross beam is preferably at least the diameter of the ring structure.

Another variant of a support structure, having a central void space, has the shape of a circular segment (region of a circle) being more than a semicircle. It is preferred that the chord of the circular segment is positioned towards the proximal end (forming a right angle with the central longitudinal axis of the blade). The central void space may be round or may have the same shape as the outer contour of the support structure.

In another embodiment the support structure can be u-shaped or having the form of a rectangular being open at one short side (preferably the proximal side) and having a rectangular central void space. The support structure can consist of two parallel lateral ribs (being parallel to the longitudinal central axis of the blade) with a third rib position in a right angle at the distal end of these ribs.

A further embodiment of the sonotrode according to the invention includes a support structure in the form of an arch. The arch may be a round arch or semi-circular arch, a parabolic arch or a catenary arch. The arch may also be a lancet arch or n equilateral pointed arch as shown here. The arch may be located on two pillars preferably located parallel to the longitudinal central axis of the sonotrode. The arch points preferably towards the distal end of the sonotrode. This means the apex is the most distally located point of the arch, which may be located on the central axis of the blade. The support structure may have a length between 3.5 and 10 mm, more preferably between 4.2 and 8 mm and the maximal thickness can be between 0.03 and 0.25 mm and preferably between 0.05 and 0.2 mm. The arch-shaped support structures may have a maximal length of 15 to 50% (preferably 18-35% and more preferred 20 to 25%) of the maximal length of the blade. The thickness of the support structure is $\frac{1}{100}$ to $\frac{1}{10}$ (preferably $\frac{1}{50}$ to $\frac{1}{20}$) of the thickness of the blade. The width is preferably less than the width of the blade. It may be between 3.5 and 5 mm.

Another variant of the support structure may be a rib along the central axis of the blade. This rib has at least two steps where the thickness decreases. The decrease is favorable a continuous decrease e.g. in form of a linear ramp, gradual slope or curve. Alternatively, the rib may be formed by two rectangles attached to the blade (two on one lateral side and two on the other side), wherein a larger rectangle is attached to the blade first and a second smaller rectangle is attached on the first rectangle. The thickness of the rib can be between 0.1 and 0.3 mm and in particular between 0.15 and 0.2 mm. The thickness of each step or rectangle can be between 0.05 and 0.20 mm. The width of the rib is preferably between 2.5 and 5 mm and preferably between 3 and 4.5 mm. The length of the rib may be between 12 mm and 18 mm. This variant is particular preferred in combination with a sonotrode of the second aspect of the present invention. It is preferred that the rib reaches from the head of the sonotrode until the distal area including the slit. Therefore, the rib may include a slit. This slit corresponds preferably to the slit of the blade. In general, there may be 2 to 5 steps or rectangles. The inventors found that sonotrodes made by additive manufacturing methods, in particular using sintering (such as selective laser sintering) have some surprising advantages. The ultrasonic surgical instrument according to the invention is regularly equipped with a line by means of which a rinsing liquid (e.g. water) can be supplied to the operating field. The surface structure generated using the afore-mentioned method of manufacturing increases the cooling efficiency by that liquid. One explanation could be that the surface structure provides for and maintain a proper liquid film on the surface of the sonotrode blade. It seems that one possible effect is that pockets created by the sintering process, which are not open to the side provide for a hydrostatic cushion. In addition, only using additive manufacturing methods it is possible to produce some of the advantageously features of sonotrodes described herein, such as the elevated structures in the depression being minimally lower than the rim and having only minimal distance between each other. In addition, using additive manufacturing allows to adapt the depth of the rim and the design of the transition from the rim to the depression or the groove extremely fine.

One embodiment of the present invention refers to a sonotrode, wherein the surface of the sonotrode or the surface of the blade has convex microstructures. The microstructures are curved or rounded outward like the exterior of a sphere or circle. Another embodiment of the present invention refers to a sonotrode, wherein the surface of the sonotrode or the surface of the blade has a roughness average Ra between 1-40 μm, preferably between 5 and 20 μm. Thereby surface roughness as a component of surface texture is quantified by the deviations in the direction of the normal vector of a real surface from its ideal form. The arithmetic average roughness, Ra is the arithmetic average value of filtered roughness profile determined from deviations about the center line within the evaluation length and the most widely used one-dimensional roughness parameter.

In general, it has been shown that it is advantageously that the distance between the highest points of the convex microstructures of the sonotrode or respectively the blade is smaller than the Amplitude. Thereby the highest point of a convex microstructure is the point of a defined hemisphere where the radius builds an angle of 90° with a longitudinal axis of the blade. In particular, the distance between the highest points of the convex microstructures in axial direction of the longitudinal blade of the sonotrode may be smaller than the amplitude. Thus, the average distance between two corresponding points on the convex structures (in particular the highest point of each convex structure) may be 20-100 μm, and preferably 40-80 μm.

Due to the surface roughness resulting from the sintering process there are point contacts between the blade and the bone. Thus, a higher energy density occurs. However, the convex surface portions, which arise by the grain size distribution, are more stable than for example roughness structures made by sandblasting.

Consequently, one embodiment of the present invention relates to a method for manufacturing a sonotrode as defined herein, wherein the sonotrode is manufactured by using additive manufacturing method. Direct Metal Laser Sintering (DMLS) or electron beam welding are such additive manufacturing processes suitable to be used to produce the sonotrodes according to the invention. Thereby the sonotrodes or the blades are built using a laser to selectively sinter (heat and fuse) a powdered metal material into layers. Subsequently a step of heat treatment may be carried out. It is preferred that the surface as resulted due to the additive manufacturing is not smoothed (evened or polished). The powder to be used may have an average particle diameter of 40-80 μm.

One embodiment of the method for manufacturing a sonotrode as defined herein refers to methods, wherein the sonotrode is built layer after layer in a way that the sonotrode grows vertically. This means the sonotrode is built upright. The proximal parts may be built first and the distal end is built last or the distal parts are built first and the sonotrode grows towards the proximal end. This has the advantage that the thickness of the layers used to build the sonotrode can vary. It is favorable that the sonotrode head is formed by layers that are less thick than the layers used for forming the blade or at least the distal parts of the blade. Using the method as described it is possible to manufacture a sonotrode that is very resistant and in particular stress resistant and on the same time has a blade having the favorable roughness and therefore favorable cutting features.

Another embodiment of the method for manufacturing a sonotrode as defined herein, refers to methods, wherein the sonotrode is built layer after layer in a way that the sonotrode grows horizontally. The sonotrode grows therefore from one lateral side to the other. This has the advantage that the resistance to bending is improved.

An alternative method suitable for manufacture of the sonotrodes or blades thereof is shot blasting or respectively shot peening. Sandblasting is less suitable. The surface structure resulting from the sintering process of metal grains cannot be entirely described by parameter such as roughness and grain size. Nevertheless, this particular surface structure has to be proven to be advantageously. Therefore, the present invention refers to a sonotrode according to the invention, wherein the sonotrode or at least the blade of the sonotrode is manufactured using additive manufacturing method such as direct metal laser sintering. In particular, the present invention refers to a sonotrode for an ultrasonic surgical instrument having a head and a distal end piece, the distal end piece being equipped as a blade for cutting bones using mechanical vibration, wherein the sonotrode or at least the blade of the sonotrode are manufactured using an additive manufacturing method such as direct metal laser sintering. In one embodiment the present invention refers to a sonotrode for an ultrasonic surgical instrument having a head and a distal end piece, the distal end piece being equipped as a planar blade with an arcuate distal end for cutting bones using mechanical vibration, wherein the sonotrode or at least the blade of the sonotrode are manufactured using an additive manufacturing method such as direct metal laser sintering. Other embodiments refer to sonotrodes being equipped or designed as described herein which are manufactured using an additive manufacturing method such as direct metal laser sintering.

Orthopedic surgeons frequently desire smoother cut surfaces than they have been able to consistently obtain by cutting or sawing a section of bone. Therefore, it is a big advantage to have a surgical instrument suitable for cutting bones and subsequently for rasping of the cut edges with the same instrument. The sonotrodes for an ultrasonic surgical instrument according to the present invention having surface roughness as defined above are not only suitable for cutting bones but may also be used to smooth the edges of a bone or respectively a bone cut. Therefore, one embodiment of the present invention refers to sonotrodes for an ultrasonic surgical instrument having a head and a distal end piece, the distal end piece being equipped as a planar blade for cutting and rasping bone (successively) using mechanical vibration. Thus, one embodiment of the present invention refers to sonotrodes for an ultrasonic surgical instrument having a head and a distal end piece, the distal end piece being equipped as a rectangular blade for cutting bone using mechanical vibration wherein the blade is further suitable as bone rasp or bone file. In another embodiment the present invention refers to a sonotrode for an ultrasonic surgical instrument having a head and a distal end piece, the distal end piece being equipped as a planar blade for cutting bones using mechanical vibration, wherein the surface of the sonotrode or the surface of the blade has a roughness average Ra between 5-40 $\mu$m. The function of a rasp is to shape, trim, and form bone surfaces or more generally from hard tissue, such as bone, cartilage and associated tissue.

In case the roughness is only used to minimize the friction it is sufficient to have a sonotrode blade with a roughness between 1 and 20 $\mu$m and in particular between 1 and 15 $\mu$m. In case the sonotrode according to the invention should be used as a file, the roughness is preferably between 10 and 100 $\mu$m. The aim of the use of a sonotrode as a file is to smooth the bone and in particular edges resulting of the cut. Therefore, an overall surface roughness is suitable. Mainly it is very useful when coarse bony areas can cause damage to surrounding tissue if they are not evened out with a file.

In addition, there may be elevated structures as described above, which are abrasive and thus, are designed and are suitable to ablate or remove unwanted bone structures such as osteophytes. Such a rasp may be used by surgeons to aid in manipulation of bone and other hard tissue surfaces for example to clean out or hollow a bone opening before the insertion of a medical implant. It can be used to scrape or file away at bone surfaces (especially cut edges) to give them a smoother finish for a variety of reasons. Using sonotrodes of the first aspect of the invention the structures of the depression support the function of a rasp of that sonotrodes. This is caused by the less elevated surfaces of the structures, which may be additionally roughened, and additional edges.

Another embodiment of the present invention refers to a method of cutting and subsequently filing or rasping bone using only one instrument. Thus, the present invention refers to a method using a sonotrode, in particular using a sonotrode according to the present invention, the method including the steps of: providing a sonotrode at an ultrasonic surgical instrument having a head and a distal end piece equipped as a planar blade, cutting a bone with the distal end piece of the sonotrode using vibration energy, turning the ultrasonic surgical instrument, the sonotrode, or the distal end piece (rotate 90 degrees) and oscillating the distal end piece so as to file or abrade bone tissue, in particular oscillating the distal end piece so as to file bone tissue from an edge or surface occurred by cutting in a preceding step.

The invention refers further to an ultrasonic surgical instrument for cutting bones, including a hand-piece containing an ultrasonic transducer and a sonotrode as defined herein being mechanically coupled to said transducer.

The term "ultrasonic surgical instrument" as used herein refers to a surgical instrument with an ultrasound transducer. This ultrasonic surgical instrument of the invention includes a sonotrode as described herein being connected to the ultrasound transducer. The ultrasound transducer may include a piezoelectric element, by means of which a high-frequency AC voltage is converted into a corresponding mechanical vibration. By way of example, the frequency of the vibration can lie between 15 kHz and 40 kHz.

Preferably, the ultrasound transducer or the housing of the ultrasonic surgical instrument of the invention and the head of the sonotrode (via the shaft of the head) are coupled to each other, wherein the shaft of the head is designed to transmit the vibration energy as fully as possible from its proximal end to the distal end piece or the blade of the sonotrode respectively.

Preferably, the material of the sonotrode according to the invention is a metallic material, such as e.g. stainless steel or titanium. The sonotrode or at least the blade thereof may be coated with titanium nitride (TiN). Thus, the present invention refers to a sonotrode for an ultrasonic surgical instrument having a head and a distal end piece, the distal end piece being equipped as a rectangular blade for cutting bones using mechanical vibration, wherein the sonotrode or at least the blade of the sonotrode is coated with titanium nitride and is preferably manufactured using an additive manufacturing method such as direct metal laser sintering.

It has been shown that the spherical microstructures on the surface of the sonotrode or respectively the blade may be deformed caused by the forces acting during cutting or rasping of the bones. Therefore, it is preferred to coat the sonotrodes or blades to harden the surface. TiN has an ideal combination of hardness, toughness, adhesion and inertness, that will not blister, flake or chip during cutting or rasping bones.

Another advantage is an optimized distribution of heat along the length of the surface created by the TiN coating. In this manner, hot spots are avoided, and the heat distribution or dispersion along the length of the surgical cutting instrument prohibits concentration of heat at the cutting edge or tips of the convex microstructures on the surface as would occur with no coating or coating only at the cutting edge.

The TiN coating may be applied by environmentally safe, Physical Vapor Deposition (PVD) vacuum system. Some processes use low temperature arc vapor deposition to deposit the titanium nitride coating, but it could also be applied by high temperature sputtering or other well-known coating processes (electron beam heating or chemical vapor deposition (CVD)). In general, pure titanium is sublimed and reacted with nitrogen in a high-energy, vacuum environment. TiN film may also be produced on Ti workpieces by reactive growth (for example, annealing) in a nitrogen atmosphere.

The TiN coating is preferably applied as a thin coating of less than 5 μm, more preferably of less than 3 μm. The thin titanium nitride coating provides the blade with a hard outer surface with a low coefficient of friction.

Preferably, the connection between the head and the vibration generator is releasable and the sonotrode including the head and the distal end piece is disposable.

The ultrasonic surgical instrument according to the invention is e.g. a hand-held device wherein a handle portion thereof houses the vibration generator being supplied with the necessary energy by a battery or through a corresponding cable connecting the hand piece to a control and supply unit. The preferred frequency for the vibration is in the ultrasonic range, preferably in the range 15 and 40 kHz or between 20 and 30 kHz and of an energy sufficient for achieving an amplitude in the micrometer range for the distal end of the perforator, between 20 and 120 μm or preferably between 60 and 100 μm.

BRIEF DESCRIPTION OF THE DRAWINGS

Exemplary embodiments of device and method according to the invention are described in further detail in connection with the appended Figures.

FIG. 14A: in top view; FIG. 14B: view to cut of the sonotrode of FIG. 14A along the axis A'; FIGS. 14C and 14D are cuts of an alternative sonotrode along a corresponding axis A'.

DETAILED DESCRIPTION OF THE INVENTION

Figure 1:
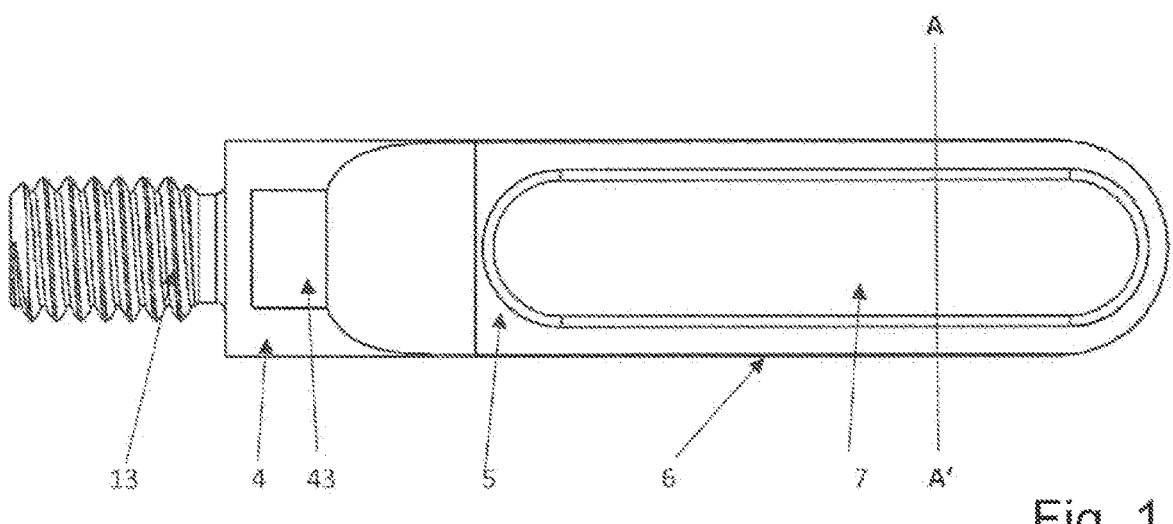
FIG. 1 shows a schematic drawing of an exemplary embodiment of an inventive sonotrode.

In all appended Figs., same reference numerals designate same elements or similar elements serving same functions.

FIGS. 1 to 10 and 14A to 51 illustrate various embodiments of sonotrodes according to the invention and including a head 4 and a distal end piece in form of a blade 5. In all FIGS. 1 to 10, the head 4 has the form of a circular cylinder with a tapering or flattened distal end 12 and a thread 13 at its proximal end. Alternatively to the thread 13, the proximal end of the head 4 may have any other structure to be able to get rigidly fixed to the housing 2 or the transducer 3 of an ultrasonic surgical instrument as illustrated in FIG. 11. The structures may be a pin or a hexagonal bolt. In addition, the head 4 of the sonotrode 1 can have one or two flat area 43 on its shell surface. Head 4 and blade 5 can be made as one piece or as two rigidly coupled pieces having one common principal longitudinal axis.

The sonotrode according to FIG. 1 includes a head 4 and a blade 5, the head having at least in its distal end region substantially the same cross section as the blade 5. Head 4 and blade 5 are designed to vibrate principally longitudinally. The blade can have an elongated, nearly rectangular shape with an arcuate distal end. It has a thin cutting edge 6.

A plane depression 7 is located on each lateral side of the blade 6. The depression may have an oval shape or rectangular shape with arcuate distal and or proximal end. The dimension of the depression 7 can be as large that it occupies most of the lateral surface of the blade 6. The depression may have a small fringe with an incline running along the circumference of the depression 7. Except this fringe the depression 7 may have no incline, thus most of the depression is plane. In addition, the depression 7 may cover nearly the entire area of the blade 5. The blade 5 may be about 20 mm in length. The thickness can be about 0.5 mm and the width about 6 mm.

Figure 2A:
FIG. 2A shows a cut of the sonotrode of FIG. 1 along the axis A-A'.

FIG. 2A shows the view to the section area along the line A-A' as shown in FIG. 1. One can see that the depression 7 may be designed so that the thickness of the blade 5 is reduced in is middle part. The depression 7 is about 1 mm deep. Thus, the thickness of the blade 5 is reduced within the area of the depressions 7 (being parallel on each lateral side of the blade 5) of about 0.3 mm.

Figure 2B:
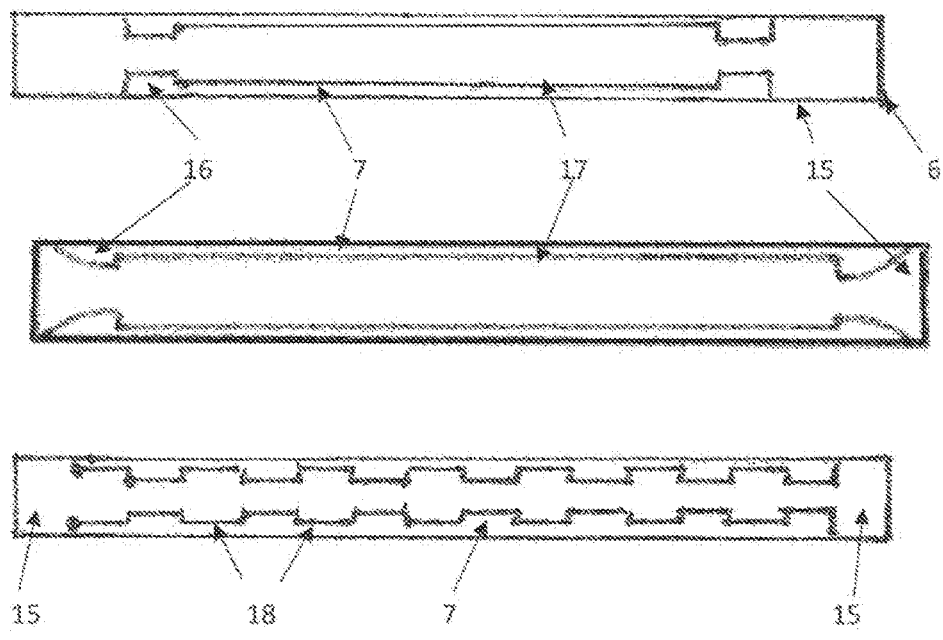
FIG. 2B shows analogues cuts of alternative embodiments of sonotrodes according to aspect one of the invention.
Figure 3:
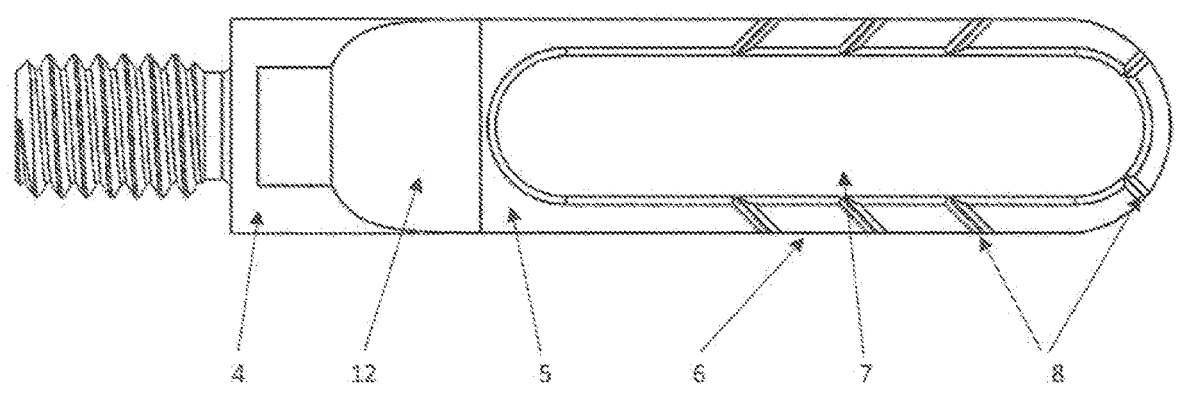
FIG. 3 shows a schematic drawing of an exemplary embodiment of an inventive sonotrode.

In FIG. 2B analogues cross sections of alternative sonotrode blades are shown. The uppermost cross section shows a rim 15, which bounds a depression 7. The depression 7 consists of a groove 16 which runs parallel to the rim 15. The area 17 within the rim 15 and the groove 16 is elevated in regard to the groove 16 but low-rise compared to the rim 15. The area 17 within the depression 7 may be between 0.1 and 5 μm lower than the rim 15. The groove 16 may be between 0.2 and 5 μm lower than the area 17. The groove 16 together with optional channels as shown in FIG. 3 ensure that a cooling liquid may be evenly distributed and that bone crisps or bone debris can escape away from the cutting area. The minimal depth of the depression 7 is sufficient to adequately lower the friction. Additionally, it is advantageously to lower the area 17 only minimal because this area may than serve as a bone file. Therefore, it is preferred that the roughness is adjusted accordingly. Therefore, the roughness Ra of the blade or at least of the area 17 is preferably between 5 and 40 μm.

The cross section in the middle shows a sonotrode blade rather similar to the one shown above. Only the rim 16 is designed differently. The rim 16 is formed with a curvature. It may also be formed parabolic. The width of the rim 15 may be reduced compared to the embodiment shown in FIG. 2A. The width of the rim may be <1 mm and preferably between 0.2-0.5 mm. The undermost drawing of FIG. 2B shows a cross section of a sonotrode blade wherein the blade has several ribs 18 within the depression 7. These ribs 18 run preferably parallel to the longitudinal axis of the blade. The ribs 18 are elevated in regard to (the lowest level of) the depression 7 but low-rise compared to the rim 15. The depression 7 may generally be between 0.2 and 5 μm lower than the rim 15. The heights of the ribs 18 may be between 0.1 and 3 μm. The minimal depth of the depression 7 (also in the area of the ribs 18) is sufficient to adequately lower the friction. Additionally, the ribs are suitable to lower lateral bending of the blade and generally make the blade more stable. The ribs reduce or even prevent fluttering of the blades. Thus, the ribs allow longer sonotrodes and respectively longer sonotrode blades of up to 60 mm. In addition the extent of the blade in the transverse direction may also be larger in case the ribs are adapted accordingly to minimize bump vibrations. There may also be other elevated structures as described herein. These structures may not only be suitable to stabilize the sonotrode and reduce unwanted lateral bending. Depending on the design the elevated structures may also or in particular be suitable for abrasion of bone, thus the sonotrode may be suitable as a rasp.

The sonotrode shown in FIG. 3 is similar to the sonotrode of FIG. 3 but the blade 5 has additional channels 8. These channels 8 run from the depression 7 to or even through the rim of the blade 5. There should be at least channels running from the depression 7 to the cutting edge 6. As shown here the channels may be equally distributed around the depression. The channels 8 may have an angular shaped (such as v-shape or square-shape) or a semicircular cross-section. The depth of the channels 8 may be the same as the depth of the depression 7. The channels are preferred in the form of oblique grooves. Thus, the channels 8 may cut the rim of the blade 5 at an oblique angle. The channels allow the bone chips to escape away from the cutting area or the area being rasp.

Figure 4A:
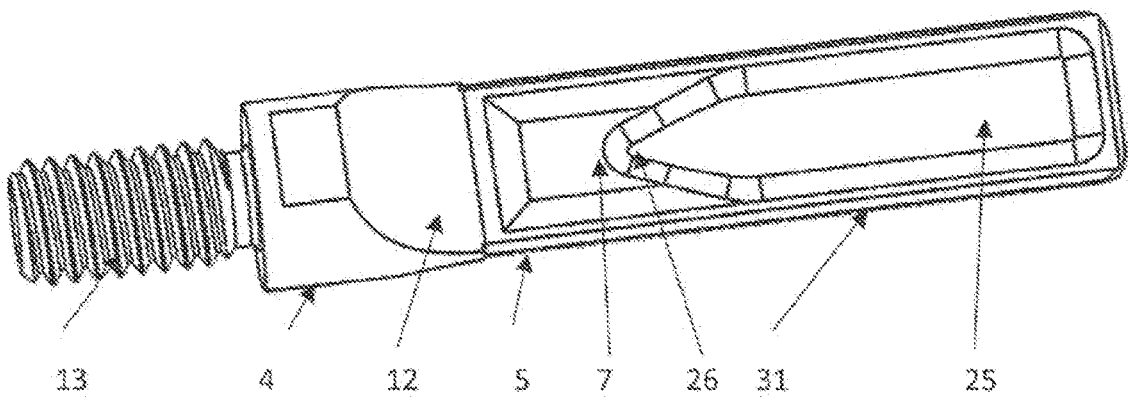
FIGS. 4A and 4B are schematic drawings of an exemplary embodiment of an inventive sonotrode.
Figure 4B:
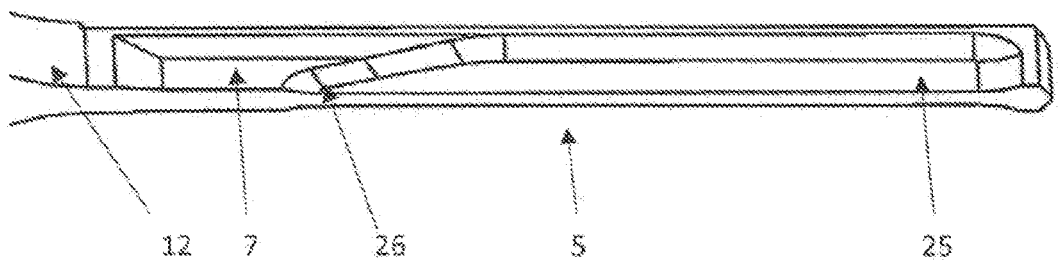

The sonotrode shown in FIGS. 4A-4B is similar to the sonotrode of FIG. 1 and FIG. 3 but the blade 5 has not an arcuate distal end but rounded corners. FIG. 4A shows a top view, wherein FIG. 4B shows a longitudinal section of the sonotrode. The distal end of the depression 7 has been adapted to the form of the blade 5. The depression 7 may have a rectangular shape with rounded corners, too. The blade has further a rectangular rim. The edge 31 and in particular the cutting edge may be rounded. It is preferred that the rounded corners and the rounded edge are built by a circular arch having a radius between 0.1 and 0.5 mm. A small radius is in particular advantageous if the sonotrode should be used to be able to penetrate the bone with said corner and cut efficiently into the cortical bone using a bent blade—otherwise the sonotrode can also have a slightly softer corner (with a radius>0.5 mm). The depression 7 may be separated into two areas, wherein the thickness of these two areas is different. There may be a second area 25 of the depression 7 which has a further reduced thickness compared to a first area of the depression. It is further preferred that said first area is rectangular or has the same shape (at least essentially) than the blade 5 and that the second area lying within these first area. Thereby the second area may have the identical distal end. The proximal end 26 of the second area 25 may have the shape of a V, wherein the apex is the most distal point. In other words, the depression 7 may have a step wherein the depth of the depression increases. This step may be symmetrical on both sides of the blade. The step may be tapered. It may be v-shaped or respectively be pointed towards the proximal end.

Figure 5:
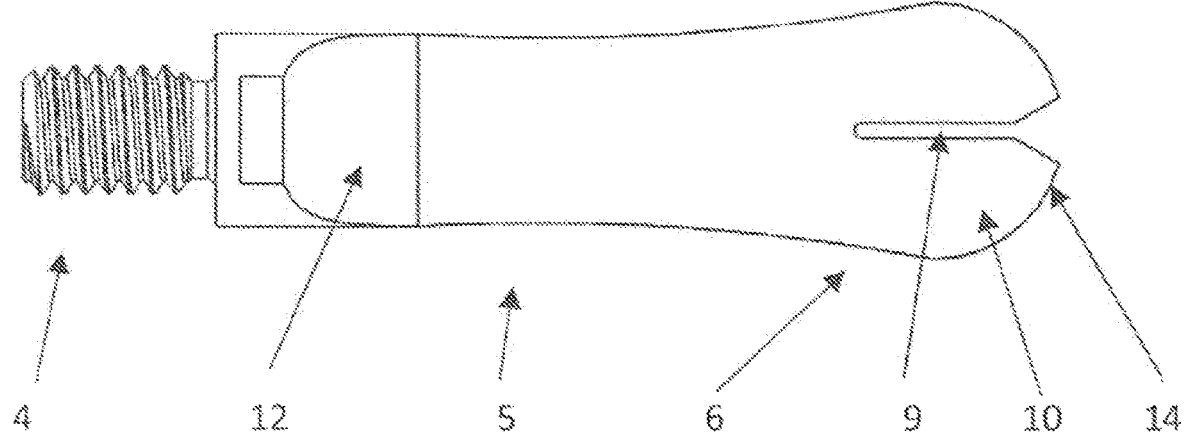
FIG. 5 shows a schematic drawing of a further exemplary embodiment of an inventive sonotrode.
Figure 6A:
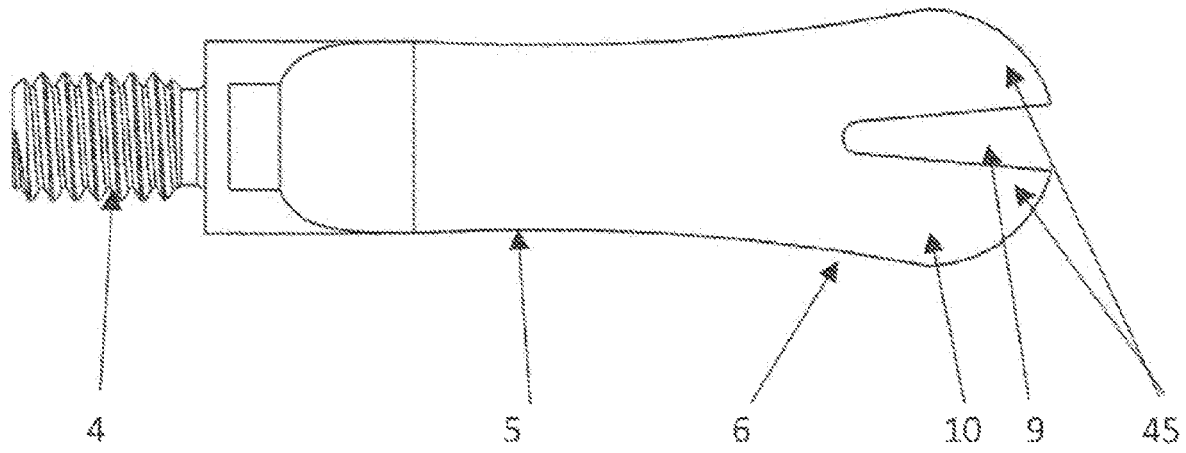
FIGS. 6A and 6B are schematic drawings of another exemplary embodiment of an inventive sonotrode.
Figure 6B:
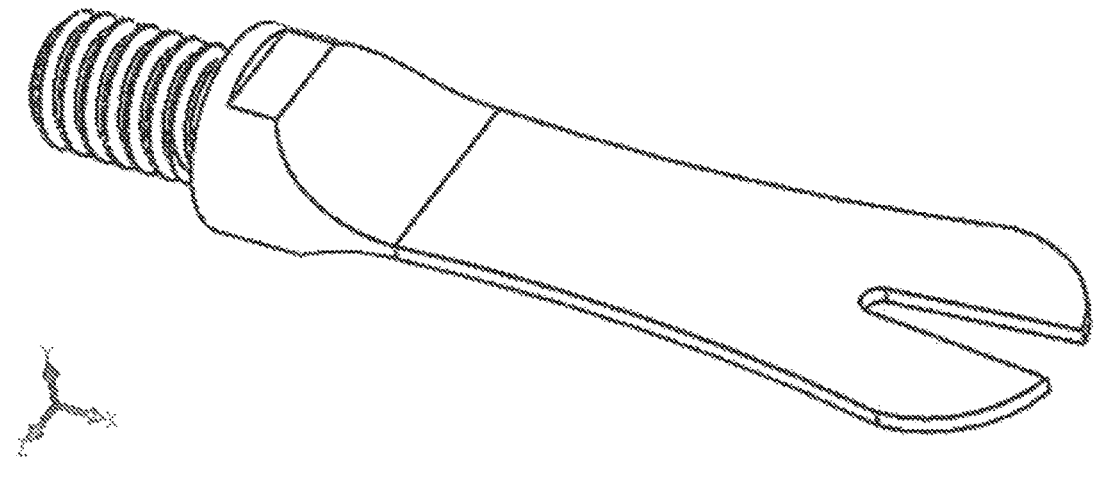
Figure 7:
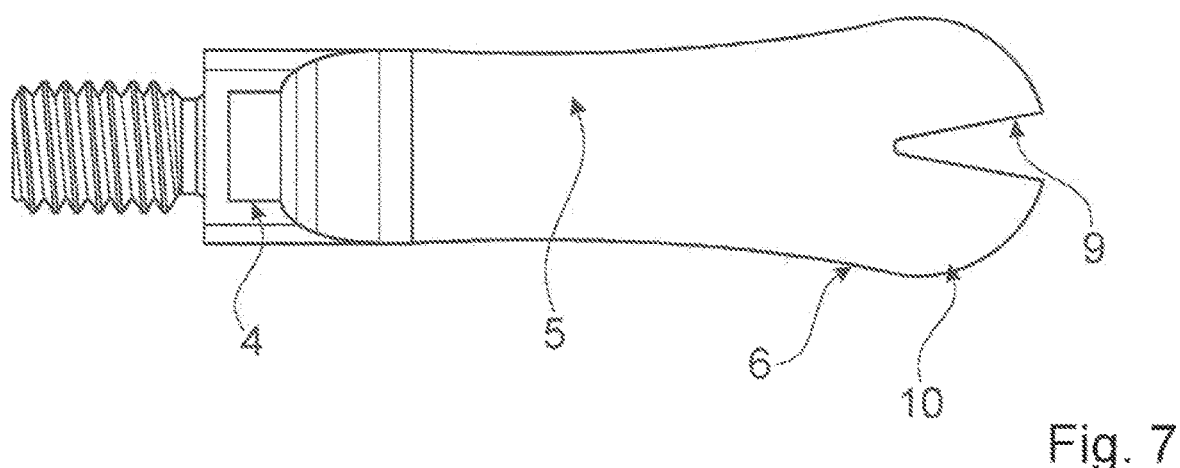
FIG. 7 shows a schematic drawing of an exemplary embodiment of an inventive sonotrode.

The sonotrodes as shown in FIGS. 5 to 7 are exemplary sonotrodes of the second aspect of the present invention. The sonotrode according to FIG. 5 includes a head 4 and a blade 5, the head having at least in its distal end region substantially the same cross section as the proximal end of the blade 5. It has a thin cutting edge 6. Head 4 and blade 5 are designed to vibrate principally longitudinally (x-axis) and in the direction of the z-axis, too. The blade can have an elongated shape with an arcuate distal end. The distal end is further broadened and has slit 9. This slit 9 runs from the most distal point of the blade or its arcuate end towards the head 4 of the sonotrode 1. Thus, the blade 5 has two symmetrical halves being separated by the slit 9. The blade 5 is about 20 mm in length. The thickness is about 0.5 mm and the width is from 6 mm at the proximal end up to 7.5 mm at the distal end. The effect of the slit in combination with the broadening is that the two resulting legs or branches 45 swing in plane towards each other. This generates beside the main amplitude a second amplitude in z-direction. This results in a scraping movement at the tips and the cutting edge which is favorable and important for effective cutting of the dense cortical bone and preventing the sonotrode from dancing on the bone but effectively cutting or "biting".

The slit 9 does not have the same length than the blade 5. It may have a quarter of the length of the blade 5 and up to a third of the length of the blade 5. The slit 9 of the sonotrode 1 according to FIG. 5 has the shape of a Y. The proximal part of the slit 9 is a narrow opening with parallel edges. The most distal part of the slit 9 widens. The edges of the slit build in the most distal part an angel between 30 and 60°.

The sonotrode shown in FIG. 6A is similar to the sonotrode 1 of FIG. 5 but the blade 5 has a slit 9 having the shape of an U. Thus, the slit is rather broad and has a blunt end. The slit 9 may cut a part out of the blade 5 having the form of a circle segment with a rounded tip. FIG. 6B shows the same sonotrode than FIG. 6A but in a three-dimensional illustration together with a coordinate system indicating the directions.

The sonotrode shown in FIG. 7 is similar to the sonotrode 1 of FIG. 5 and FIGS. 6A-6B, but the slit 9 in the blade 5 is shorter and has the shape of a V.

Figure 8:
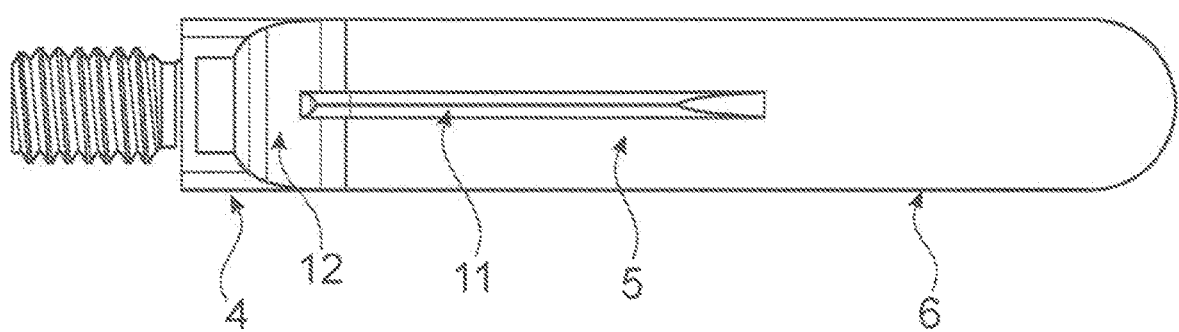
FIG. 8 shows a schematic drawing of an exemplary embodiment of an inventive sonotrode.
Figure 9:
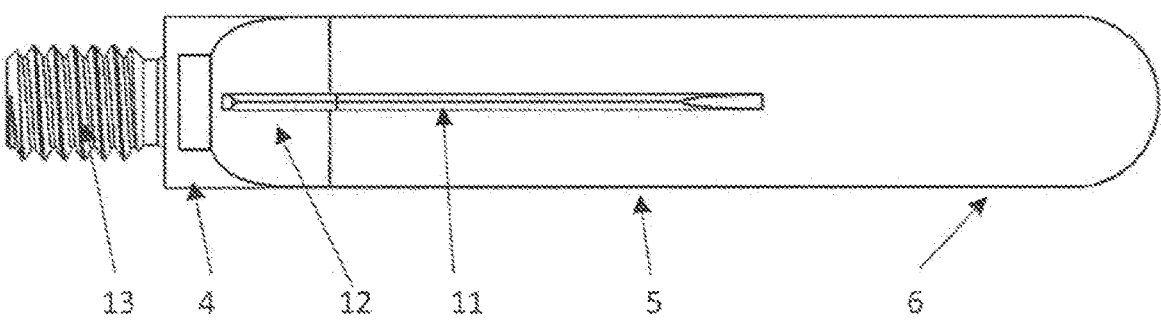
FIG. 9 shows a schematic drawing of a further exemplary embodiment of an inventive sonotrode.
Figure 10:
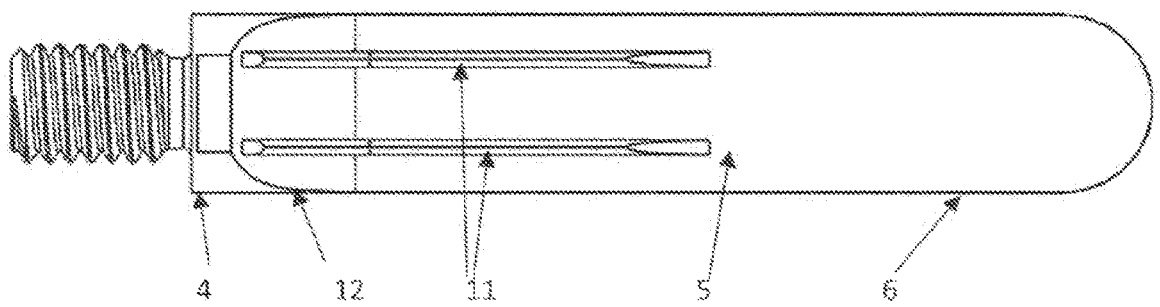
FIG. 10 shows a schematic drawing of an exemplary embodiment of an inventive sonotrode.
Figure 11:
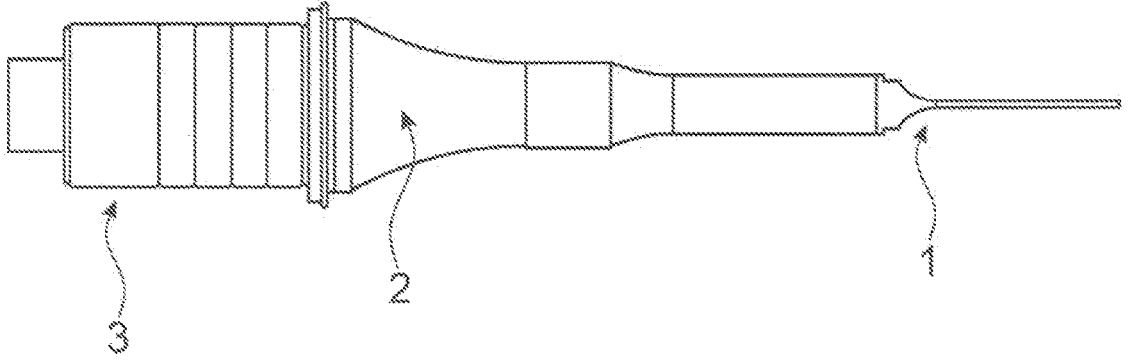
FIG. 11 shows the distal part of an ultrasonic surgical instrument for cutting bones including a piezoelectric stack located inside a housing with a sonotrode at the tip of the housing.

The sonotrodes as shown in FIGS. 8 to 10 are exemplary sonotrodes of the third aspect of the present invention. The sonotrode according to FIG. 8 includes a head 4 and a blade 5, the head having at least in its distal end region substantially the same cross section as the proximal end of the blade 5. It has a thin cutting edge 6. Head 4 and blade 5 are designed to vibrate principally longitudinally. The blade 5 is about 30 mm in length. The thickness is about 5.5 mm and the width is about 6 mm.

Nonetheless of the rather long blade, torsion should be avoided. The blade 5 has a rib 11 running along the longitudinal middle axis of the blade 5. The rib 11 may be shorter than the blade 5. The rib 11 may start at the flattened distal portion 12 of the head 4 and ends in the middle third of the blade 5. The rib 11 may have a flattened ends. The rib 11 can have a semicircular cross section or an angular cross section. The width and thickness of the rib 11 may be around 0.5 mm or even less. The blade 5 may have a rib 11 on both lateral sides. The ribs on the different sides may be symmetrically arranged, in fact axisymmetric to the central axis. This means the ribs 11 have corresponding positions on each side of the blade 5.

The sonotrode shown in FIG. 8 is similar to the sonotrode of FIG. 7 but the rib 11 is longer and thinner. The rib 9 starts at the proximal end of the flattened area 12 of the head 4. The rib 11 can have a semicircular cross section or an angular cross section. The width and thickness of the rib 11 may be around 0.2 mm. The rib 11 has a flattened distal end.

The sonotrode shown in FIG. 9 is similar to the sonotrode of FIG. 8 but the blade 5 has two ribs 11 on each lateral side, which means there are in total four ribs 11. All these ribs 11 run along a longitudinal axis of the blade 5.

The ribs as shown in FIG. 10 results in a new distribution of the bending forces impinging on the blade. The maximal stress is located at the proximal ends of the ribs. Nevertheless, the forces are distributed along the length of the ribs.

FIG. 11 shows the distal part of an ultrasonic surgical instrument including a transducer, such as a piezoelectric stack 3 located inside a housing 2 with a sonotrode 1 at the tip of the housing. The sonotrode 1 has been attached to the housing 2 via its proximal end of the head. Therefore, the head may have a thread or a known alternative connector at its proximal end.

The sonotrodes of FIGS. 14A-D show embodiments according to aspect 4 of the invention. The sonotrodes include a head 4 and a distal end piece in form of a blade 5. The head 4 has the form of a circular cylinder with a tapering distal end 12 and a pin at its proximal end. Alternatively to the pin the proximal end of the head 4 may have any other structure to be able to get rigidly fixed a housing or a transducer of an ultrasonic surgical instrument. Head 4 and blade 5 are made as one piece or as two rigidly coupled pieces having one common principal longitudinal axis. The head 4 having at least in its distal end region substantially the same cross section as the blade 5. The blade 5 is designed to be suitable for abrading a bone more than cutting. Therefore, the blade is arched or bent. The blade can have an elongated, nearly rectangular shape with a flattened distal end constructed as a cutting edge 6. These sonotrodes are used in axially movements to scrape out bone structures in corners or foramina (e.g. to cut osteophytes to allow decompression).

Figure 14A:
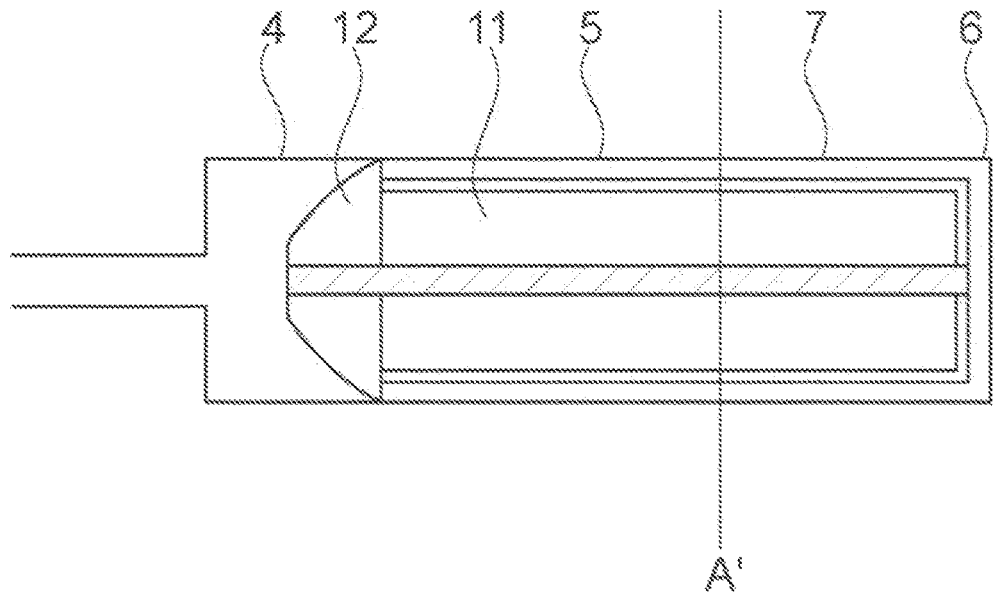
FIGS. 14A-14D are schematic drawings of an exemplary embodiment of an inventive sonotrode.
Figures 14B, 14C:
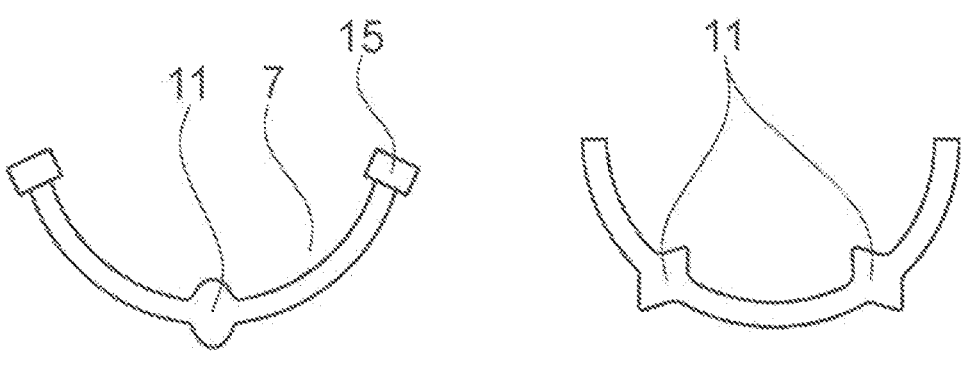

FIG. 14A shows a top view of one embodiment according to aspect 4 of the invention and FIG. 14B a cut thereof along the axis labelled A'. A plane depression 7 may be located on each lateral side of the blade 5. The depression may have an oval shape or rectangular shape. The dimension of the depression 7 can be as large that it occupies most of the lateral surface of the blade 5. The depression may have a small fringe 15 with an incline running along the circumference of the depression 7. The blade 5 is about 20 mm in length. The thickness is about 0.5 mm and the width is about 6 mm. The blade 5 has two ribs 11 running along the longitudinal middle axis of the blade 5. The rib 11 may start at the flattened distal portion 12 of the head 4 and ends at the cutting edge of the blade 5, which is the flattened distal end. The rib 11 can have a semicircular cross section or an angular cross section. The thickness of the rib 11 can be chosen to be the same than the thickness of the rim 15. The ribs on the different sides may be symmetrically arranged, in fact axisymmetric to the central axis. This means the ribs 11 have corresponding positions on each side of the blade 5.

Figure 14D:
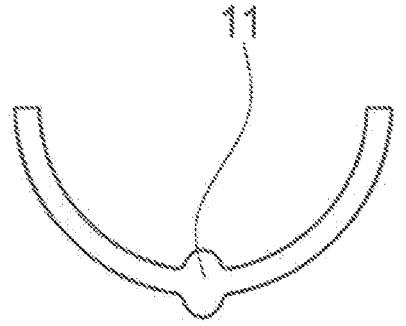

FIG. 14C shows a cut of an alternative blade 5 of a sonotrode according to aspect 4 of the invention along a corresponding axis line A'. This blade 5 has no depression but 2 ribs 11 on each lateral side, which means there are in total four ribs 11. All these ribs 11 run along a longitudinal axis of the blade 5. The cross section of the ribs may be triangular, wherein the corners are rounded. FIG. 14D shows a cut of another alternative blade 5 of a sonotrode according to aspect 4 of the invention along a corresponding axis line A' without a depression. The cross section of the rib may be semicircular, wherein the transition between rib and blade surface is not abrupt but continuously in form of a curvature.

Figure 15:
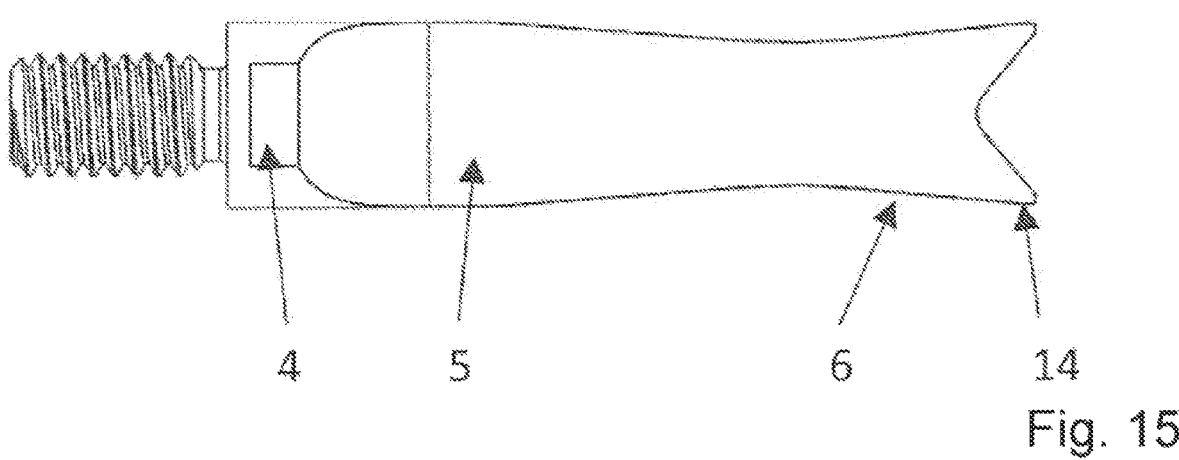
FIG. 15 shows a schematic drawing of an exemplary embodiment of an inventive sonotrode.
Figure 16:
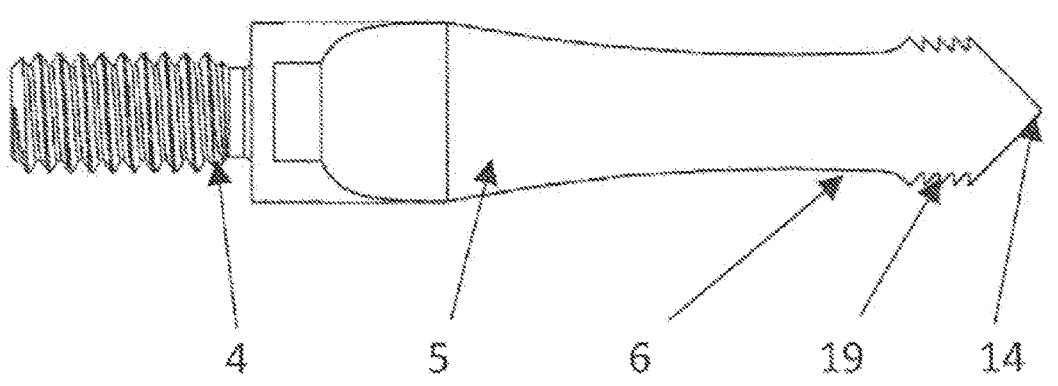
FIG. 16 shows a schematic drawing of an exemplary embodiment of an inventive sonotrode.

FIGS. 15-18 show top views of embodiments according to the invention, wherein the sonotrode blade has at least one peak at its distal end. With the aid of the peak or sharp point the blade may scratch the cortex of the bone to be cut and facilitates the penetration of the bone. FIG. 15 shows a sonotrode with a head 4 and a blade 5 wherein the distal end has two peaks 14 formed at the distal end of the cutting edge and the opposite side. Therefore, the distal side of the sonotrode has a wedge-shaped cut out. The blade of the sonotrode may be slightly waisted having the narrowest part after two third of the length (from the proximal to the distal end). It is preferred that the peaks 14 are built by a circular arch having a radius between 0.1 and 0.5 mm. The sonotrode as shown in FIG. 16 has a blade 5 which is narrowed towards the distal end and includes a peak at its distal end. This peak is formed by a distal end having an arrowhead-shape. In addition, the blade may optionally have barbs 19 at the distal end of both lateral edges or of the cutting edge, only. This sonotrode is optimized to be able to cut deeply into a dense bone (e.g. a bone having a wide cortical area. The barbs are able to abrade material on the return movement of the blade when cutting by sawing movements. The waist allows to tilt the blade in the plane and thus to grip deeper into the bone and to minimize friction.

Figure 17:
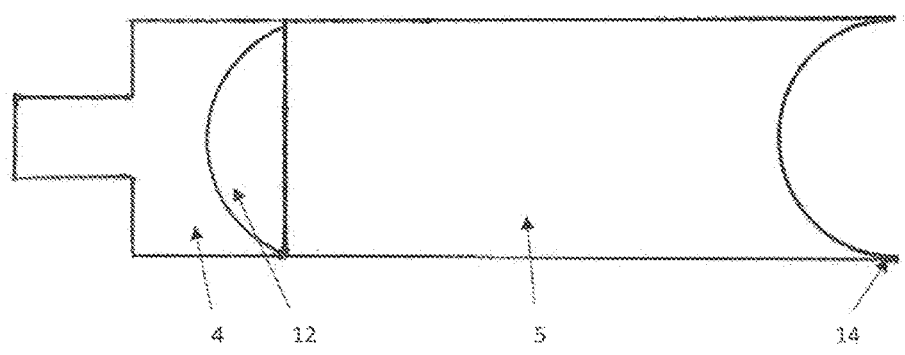
FIG. 17 shows a schematic drawing of an exemplary embodiment of an inventive sonotrode.

FIG. 17 shows a sonotrode with a blade 5 having a distal end being dovetail shaped. The distal side of the sonotrode bade is formed as a concave circular line. This results in two sharp peaks at the distal end of the lateral edges.

Figure 18:
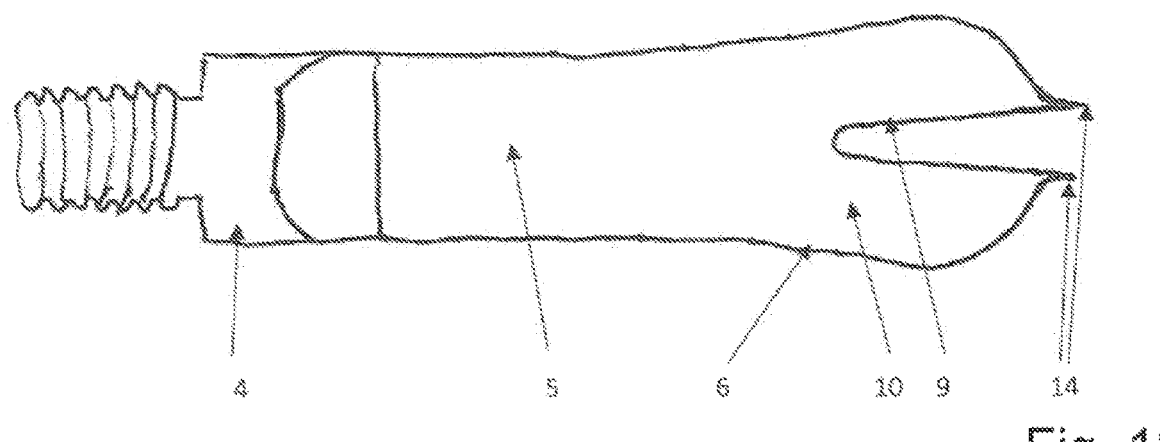
FIG. 18 shows a schematic drawing of an exemplary embodiment of an inventive sonotrode.

FIG. 18 shows a sonotrode according to the second aspect of the present invention. The two distal ends of the slit 9 are extended distally. Thus, two sharp peaks 14 result. It may be that only one end of the slit 9 is extended and forms a sharp peak 14. In case that both ends are extended to form peaks they may have the same length but alternatively the length of the extension may vary.

Figure 19:
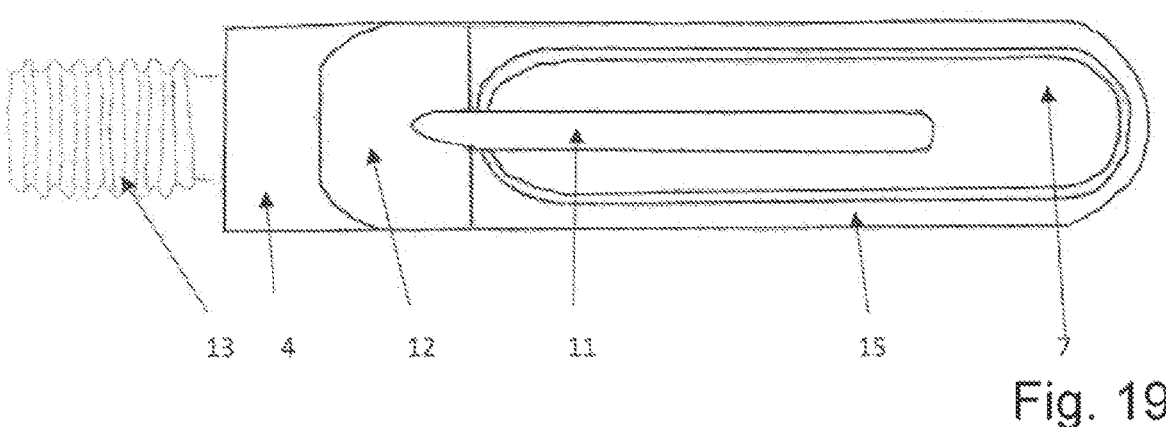
FIG. 19 shows a schematic drawing of an exemplary embodiment of an inventive sonotrode.

FIG. 19 shows a sonotrode according to the first aspect of the invention having a head 4 with a thread 13 and a blade. The blade has a depression 7 bounded by rim 15. To increase the stiffness of the blade the sonotrode includes a rib 11. This rib 11 may start in a flattening area 12 of the head 4. The height of the rib 11 is chosen so that the rib 11 does not protrude over the rim 15. It is preferred that the rib 11 is raised compared to the level of the depression 7 but is lower than the rim 15. It is possible that the rib 11 ends at the distal end of the depression 7. As shown here the rib 11 may also be shorter than the length of the depression 7.

Figure 20A:
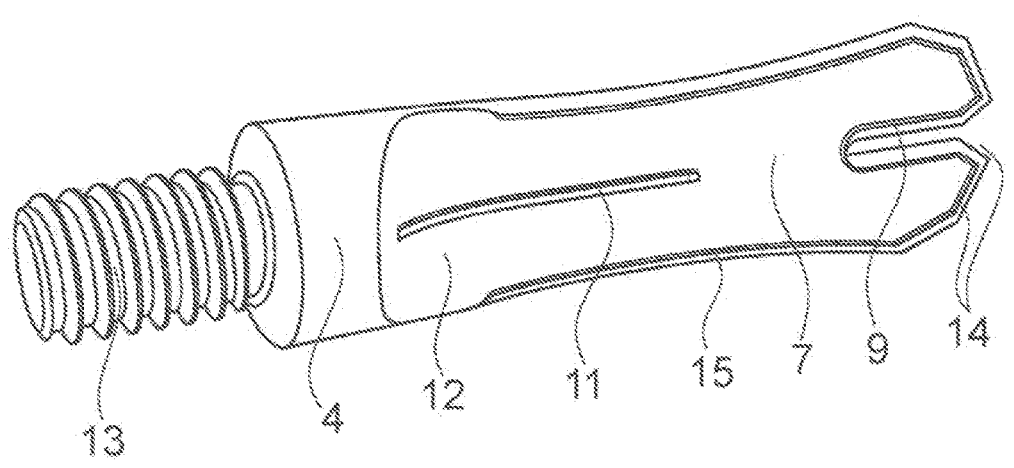
FIGS. 20A-20C are schematic drawings of an exemplary embodiment of an inventive sonotrode.

FIG. 20A shows a sonotrode according to the present invention which has features of different aspects of the invention (first, second and third aspect) having a head 4 with a thread 13 and a blade. The sonotrode has a slit 9. The distal end besides the slit is not rounded but has different facets. Thus, three or more peaks 14 results in each half of the distal end. It may be that only one half of the distal end (e.g. between the slit 9 and the cutting edge) is not rounded but cut into facets. In case that both ends are cut to form facets they may have the same number of facets but alternatively the number of facets may vary. The blade has further a depression 7 bounded by rim 15. To increase the stiffness of the blade the sonotrode includes a rib 11. This rib 11 may start in a flattening area 12 of the head 4. The height of the rib 11 is preferably chosen so that the rib 11 does not protrude over the rim 15.

Figure 20B:
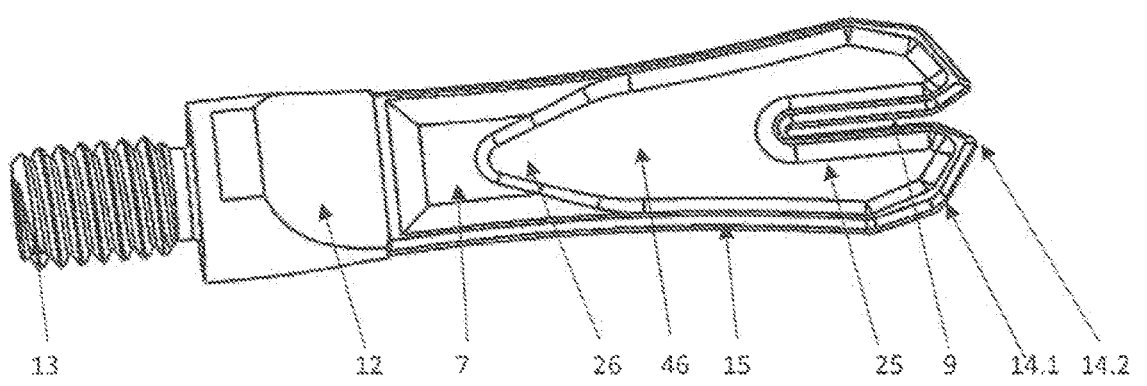
Figure 20C:
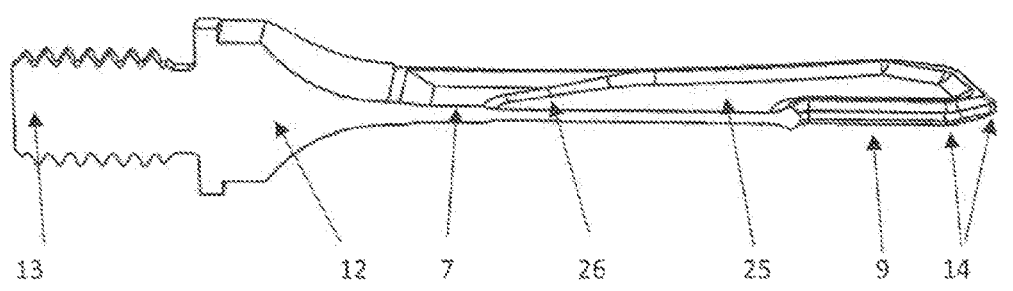

FIG. 20B shows a variation of the sonotrode according to Figure FIG. 20A. The flexural movement of the sonotrode could be minimized. In general, the edges and peaks 14 have been smoothened. This means the rim 15 is rounded and the peaks 14 are rounded tips. In addition, the depression 7 has a first proximal area and a second distal area 46, wherein the first area has a reduced depth compared to the second area. The proximal end of the second area points to the proximal end of the blade. FIG. 20C shows a longitudinal section of the sonotrode according to FIG. 20B. As can be seen the rim around the depression 7 is rounded or curved. Alternatively, to the embodiment shown, the rim of the depression 7 at the proximal end may be wider than the rim at the distal end and the depression 7 may have a v-shaped proximal end pointing towards the head of the sonotrode. The translation from the rim to the depression may be s-shaped or formed continuously. The outer edges have a phase of 45°. The transition from the rim to the proximal area of the depression has rounding with a radius of 5 mm. The step to the distal area 46 of the depression has a rounding with a radius of 1 mm. The outer corners 14.1 have a radius of 1 mm and the peaks 14.2 besides the slit are rounded with a radius of 0.2 mm. The maximal thickness of the blade is 0.8 mm, the thickness within the proximal area of the depression is 0.6 mm and the minimal thickness (within the area 46) is 0.4 mm.

Figure 21A:
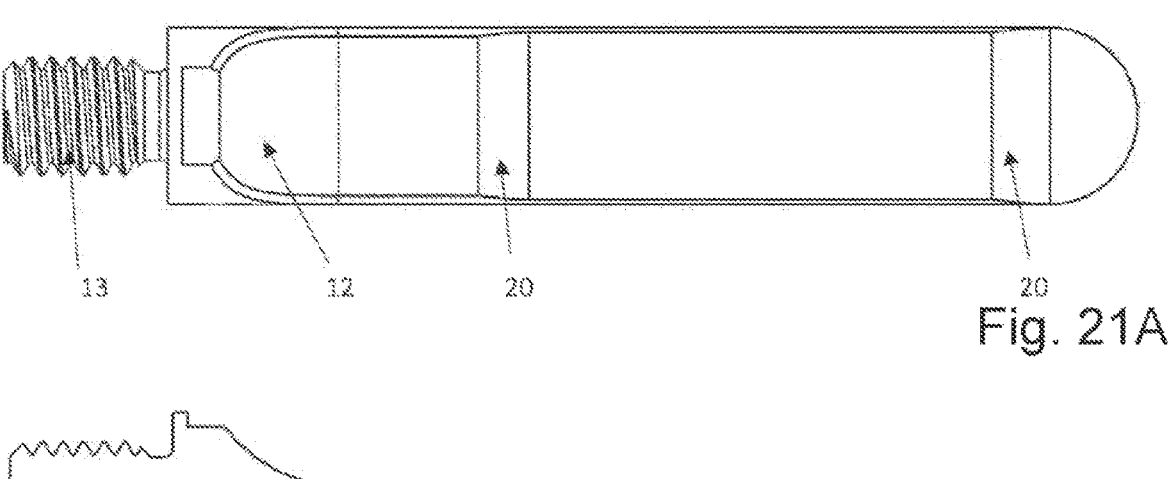
FIGS. 21A-21B are schematic drawings of an exemplary embodiment of an inventive sonotrode.
Figure 21B:
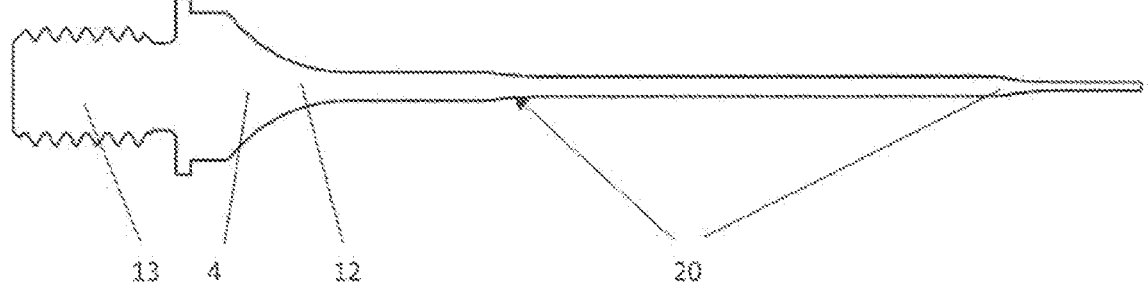

FIG. 21A shows a sonotrode according to the fifth aspect of the invention having a head 4 with a thread 13 and a blade. The blade has at least one step 20. Each step includes a tapering of the thickness of the blade. Thus, each step defines two different levels, one located proximally and one located distally of the step. Thereby, the distal level is defined by a thickness being less than the thickness of the proximal level. The decrease in thickness is preferably symmetrical. In addition, the step may be a region of continuous tapering. Alternatively, the step may be built by two surfaces forming a right angle, like a stair step. FIG. 21B shows a longitudinal section of the sonotrode according to FIG. 21A. Steps 20 are illustrated. These steps are preferably tapered.

Figure 22A:
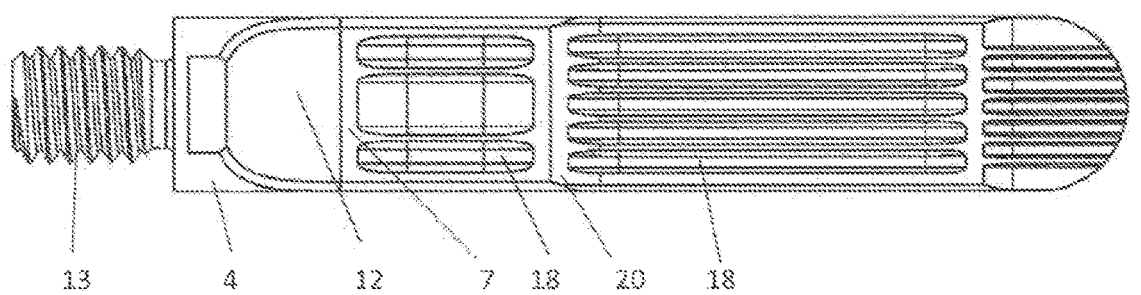
FIGS. 22A-22B are schematic drawings of an exemplary embodiment of an inventive sonotrode.
Figure 22B:
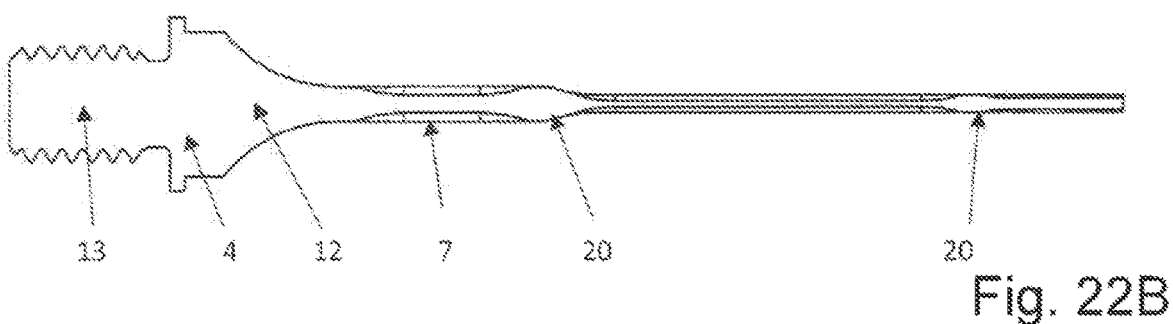
Figure 23A:
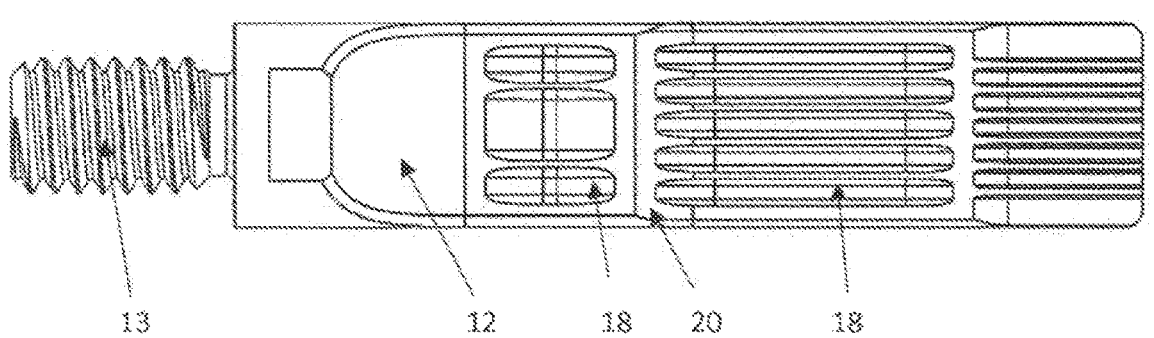
FIGS. 23A-23B are schematic drawings of an exemplary embodiment of an inventive sonotrode.
Figure 23B:
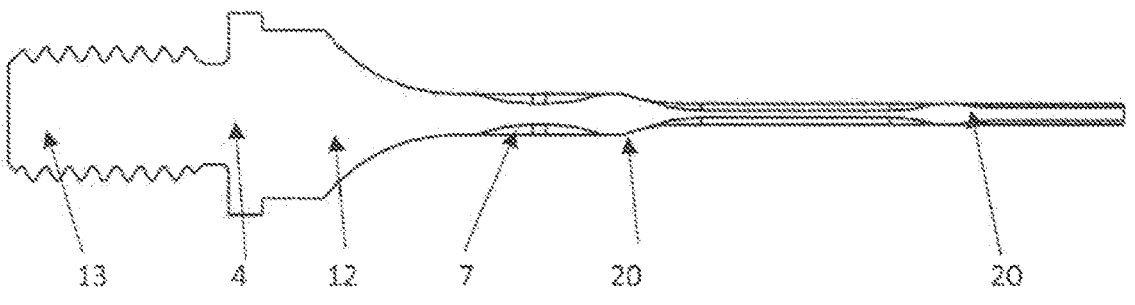

FIGS. 22A and 23A each show a sonotrode according to the fifth aspect of the invention having a head 4 with a thread 13 and a blade. The blade has two steps 20. The blade of the sonotrode according to FIG. 22A has a distal end being arcuate wherein the blade of the sonotrode according to FIG. 23A has rounded ends. The levels distal and proximal of a step differs in thickness. The blade is becoming thinner with each step. In addition, the levels may differ further. A level may include a lateral depression 7 and ribs 11. The ribs run preferably parallel to each other and parallel to the longitudinal axis of the sonotrode blade. The number and/or arrangement of the ribs may differ. The distal level being thinner may include more ribs than the proximal level. The ribs increase the stability of a thin sonotrode. In addition, the surface coming into contact with the bone to be cut is less. This reduces the friction. Less friction means a reduction of heat. Further the risk that the blade gets stuck within the bone cut is minimized. FIG. 22B and FIG. 23B show each a longitudinal section of the sonotrode according to FIG. 22A or 23A, respectively.

Figure 24A:
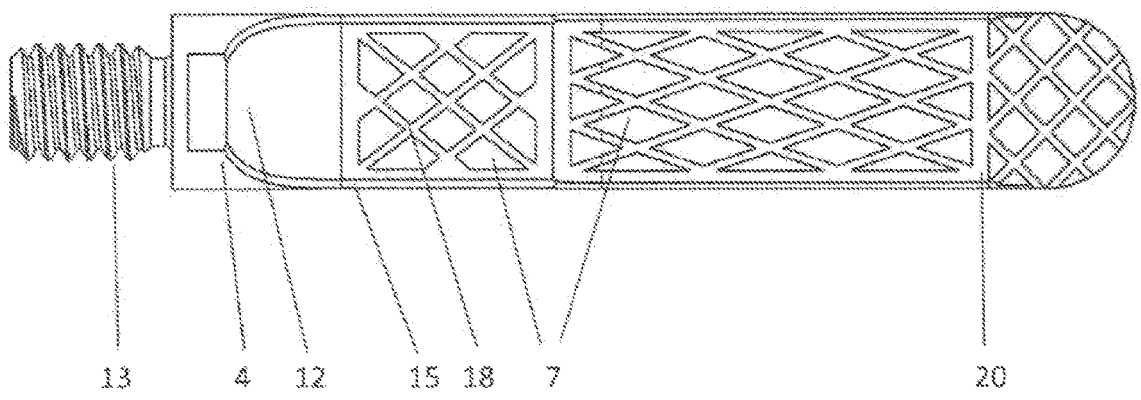
FIGS. 24A-24B are schematic drawings of an exemplary embodiment of an inventive sonotrode.
Figure 24B:
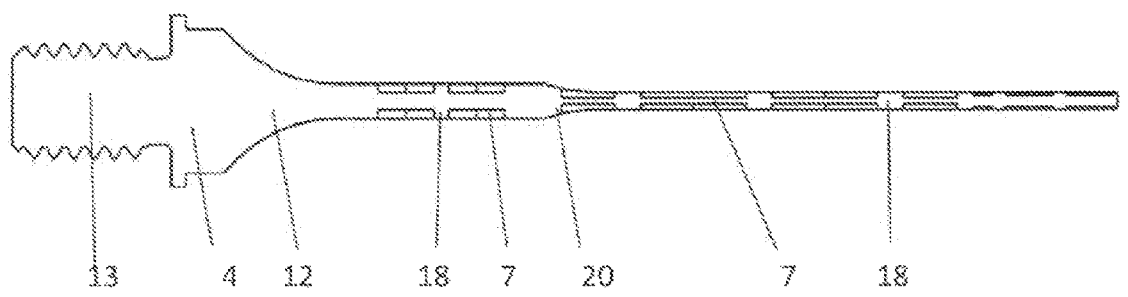

FIG. 24A shows a sonotrode similar to the sonotrodes of FIGS. 22A and 23A. The blade has two steps 20, too. Furthermore, two areas of reduced thickness 7 of the sonotrode being separated by the first (proximal) step and having an elevated structure made of ribs 20 being arranged to form a grid. It is preferred that the cross section of the elevated structure and in particular of the ribs 11 is selected in a way that the structure (or rib) does not protrude above the rim 15 surrounding the depression 7. The most distal level may have ribs 11, which can form a grid or run parallel to each other but no area of reduced thickness. FIG. 24B shows a longitudinal section of the sonotrode according to FIG. 24A.

Figure 25:
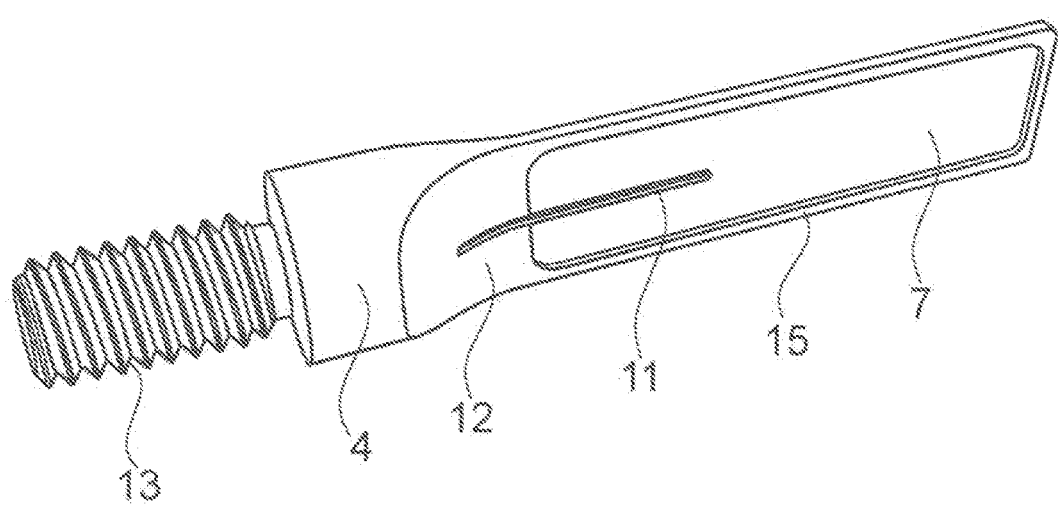
FIG. 25 shows a schematic drawing of an exemplary embodiment of an inventive sonotrode.

FIG. 25 shows a sonotrode according to aspect 1 and 3 of the invention. The blade can have an elongated, nearly rectangular shape with a flattened distal end constructed as a cutting edge. A plane depression 7 may be located on each lateral side of the blade. The depression may have a rectangular shape. The dimension of the depression 7 can be as large that it occupies most of the lateral surface of the blade. The depression may have a small rim 15 running along the circumference of the depression 7. The blade has two ribs 11 running along the longitudinal middle axis of the blade. The ribs 11 may start at the flattened distal portion 12 of the head 4 and ends within the proximal half of the blade. The ribs 11 can have a semicircular cross section or an angular cross section. The thickness of the rib 11 can be chosen to be the same than the thickness of the rim 15. Ribs on both sides may be symmetrically arranged, in fact axisymmetric to the central axis. This means the ribs 11 have corresponding positions on each side of the blade.

Figure 26:
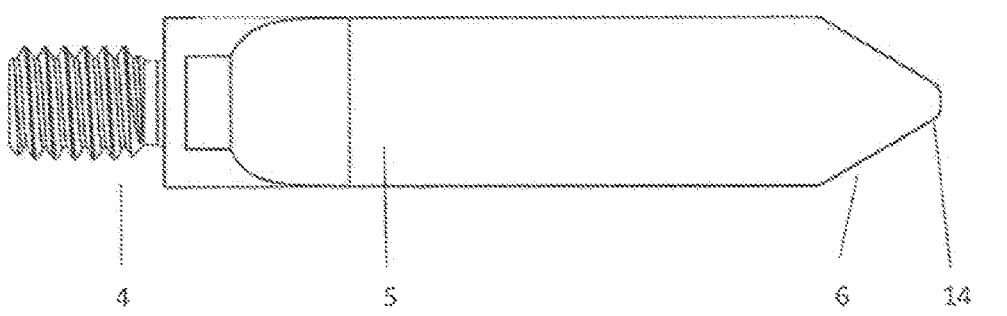
FIG. 26 shows a schematic drawing of an exemplary embodiment of an inventive sonotrode having a peak at its distal end.

The sonotrode according to FIG. 26 includes a head 4 and a blade 5, the head having at least in its distal end region substantially the same cross section as the blade 5. Head 4 and blade 5 are designed to vibrate principally longitudinally. The blade can have an elongated, nearly rectangular shape with a distal end that has the shape of an arrow head. In other words, the distal end of the blade has a peak 14 ending on the longitudinal central axis or the blade is shaped like an arrow. It has a thin cutting edge 6. The sonotrode according to FIG. 26 allows for finer cuts than blades with a rounded distal end. A plane depression 7 may be located on each lateral side of the blade 6.

Figure 27:
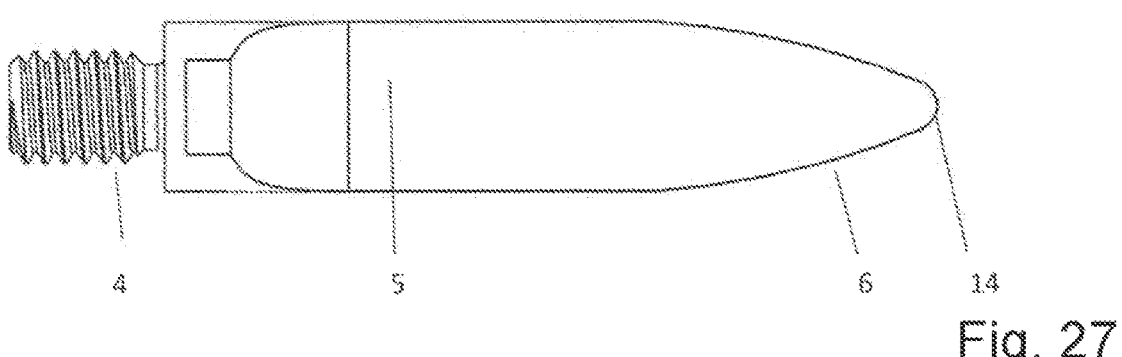
FIG. 27 shows a schematic drawing of an exemplary embodiment of an inventive sonotrode.

The sonotrode according to FIG. 27 is similar to the one of FIG. 26. It differs in the lateral edge. The lateral edge and in particular the cutting edge 6 is more curved. There is no corner point formed by the lateral edge and the lateral side of the arrowhead. There is a smooth transition.

Figure 28:
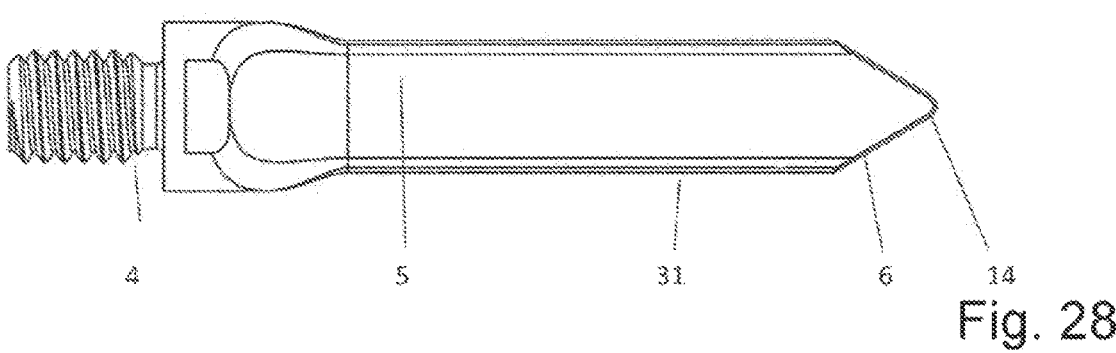
FIG. 28 shows a schematic drawing of an exemplary embodiment of an inventive sonotrode.

The sonotrode according to FIG. 28 shows a further embodiment of a sonotrode with a distal end having the shape of an arrowhead. The lateral edges are rounded and the blade 6 of the sonotrode has reduced width along the whole blade compared to the distal end of the sonotrode head 4. The blade 6 is slender than the sonotrode head 4.

Figure 29:
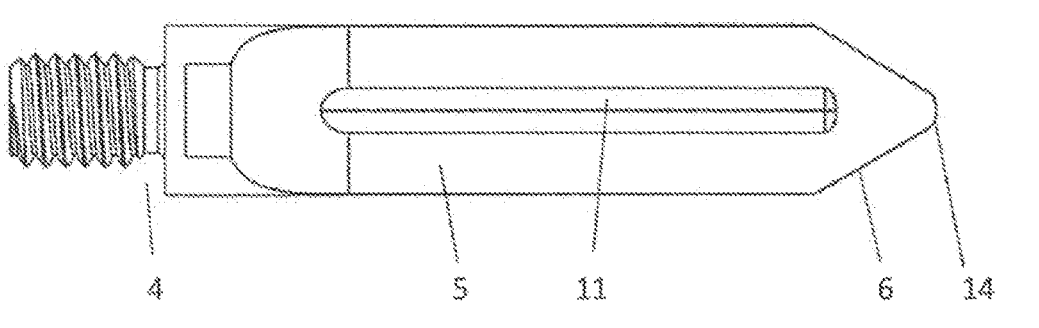
FIG. 29 shows a schematic drawing of an exemplary embodiment of an inventive sonotrode.

The sonotrode according to FIG. 29 is similar to the one of FIG. 26. It differs in a curved rib 11 along the blade 6. The rib should end within the arrow head. The thickness of the rib is up to 0.15 mm (at the line of maximal thickness) and more preferred up to 0.12. The width of the rib is between 1.2 and 2 mm and preferred between 1.4 and 1.8 mm. The cross-section of symmetrical ribs 11 at the two lateral sides of the blade is "lemon-shaped". The ribs reduce the maximal stress when oscillation is used.

Figure 30:
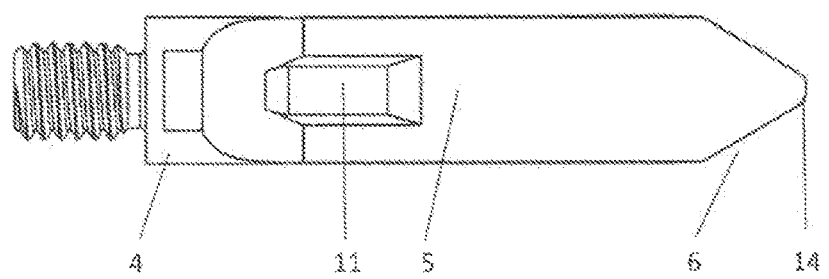
FIG. 30 shows a schematic drawing of an exemplary embodiment of an inventive sonotrode with a support structure.

The sonotrode according to FIG. 30 is similar to the one of FIG. 26. It differs in a short but broad rib 11 on the proximal end of the blade 6. The rib may be attached to the head of the sonotrode and may have a length between 2 and 5 mm, more preferably between 2.5 and 4.5 mm. The width of the rib may be between 1.5 and 2.5 mm and the maximal thickness can be between 0.03 and 0.12 mm. The bending forces affecting the blade are better distributed compared to the same blade without the rib 11. Points of maximal stress are the proximal part of the rib, the distal flattening of the rib and points lateral to the distal corners of the rib. This results in reduced maximal stress and decreases the risk for breaking of the blade.

Figures 31A, 31B:
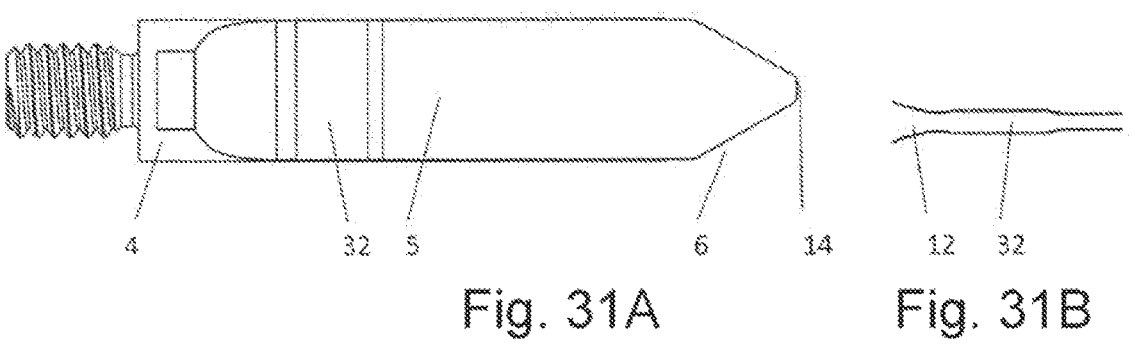
FIGS. 31A-31B are schematic drawings of an exemplary embodiment of an inventive sonotrode with a support structure.

The sonotrode according to FIG. 31A is similar to the one of FIG. 26. It differs in a thickening at the proximal end of the blade 5. The FIG. 31A shows a top view whereas FIG. 31B illustrates a longitudinal section of the sonotrode according to FIG. 31A. The thickening reaches from one lateral end to the other lateral end, thus encompasses the maximal with of the blade. The proximal and distal end may be flattened (continuous translation). It may have a length between 2 and 5 mm, more preferably between 2.5 and 4.5 mm and the maximal thickness can be between 0.03 and 0.12 mm. The thickening shifts the stress pattern forward and reduces the maximal stress when oscillation is used.

FIGS. 32 to 44 show embodiments of a sonotrode similar to the one of FIG. 26. The blades 6 of the sonotrodes have different shaped thickening 32 at the proximal end of the blade 6, which serves as distributors for the stress resulting from bending forces during vibration because of ultrasound. It is thereby preferred that the thickenings or support structures are attached symmetrically on both sides of the blade. The thickenings as shown here can be part of each sonotrode according to the present invention. The shown embodiment of the blade design is only an example illustrating the thickening.

Figure 32:
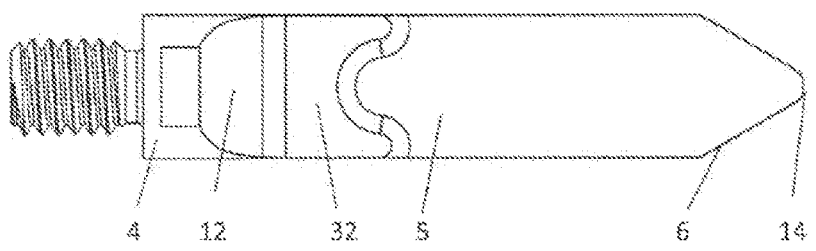
FIG. 32 shows a schematic drawing of an exemplary embodiment of an inventive sonotrode with a support structure.

The thickening or support structure 32 of the sonotrode shown in FIG. 32 reaches from one lateral end to the other lateral end, thus encompasses the maximal with of the blade. The proximal and distal end may be flattened (continuous translation). The distal end of the structure 32 has elongated, rounded ends at the borders. The distal end of the structure 32 may be wave shaped, whereby a wave through is positioned on the central axis of the sonotrode. The thickening 32 may have a length between 2.5 and 5.5 mm, more preferably between 3.5 and 5 mm and the maximal thickness can be between 0.03 and 0.12 mm.

Figure 33:
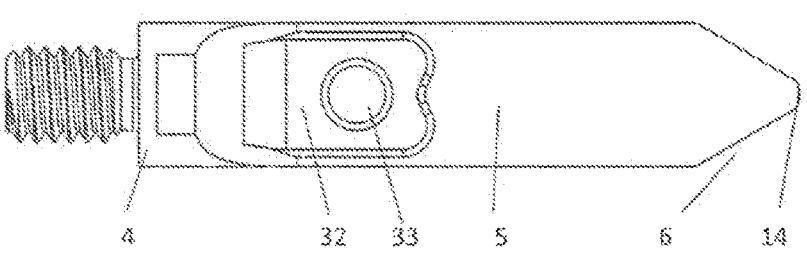
FIG. 33 shows a schematic drawing of an exemplary embodiment of an inventive sonotrode with a support structure.

The thickening or support structure 32 of the sonotrode shown in FIG. 33 has the shape of a frame around a circular void space 33 (or circular hole). The circular void space is positioned central on the central axis of the blade. The frame closing around the void. The frame may have a wave shape at its distal end. It has preferably less width than the blade. It may have contact to the distal end of the sonotrode head 4. The proximal and distal end may be flattened (continuous translation). The thickening 32 may have a length between 3 and 7 mm, more preferably between 4 and 6.5 mm and the maximal thickness can be between 0.03 and 0.12 mm. The bending forces acting on the blade are more distributed compared to the blade without support structure 32. Points of maximal stress are the points of the ring located lateral to the void space and a strap-shaped area distal of the support structure. This results in reduced maximal stress (about 20%) and decreases the risk for breaking of the blade.

Figure 34:
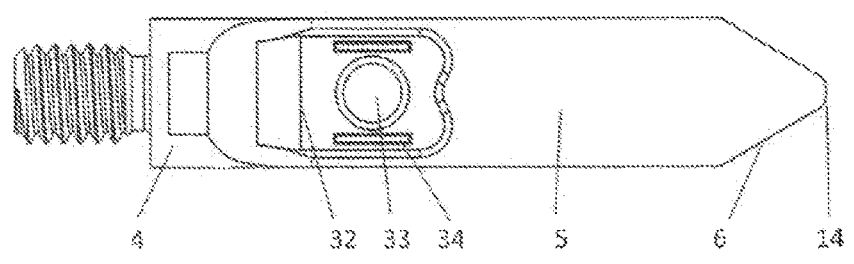
FIG. 34 shows a schematic drawing of an exemplary embodiment of an inventive sonotrode with a support structure.

In FIG. 34 the support structure 32 has additional bars 34 being superimposed lateral (from proximal to distal) of the circular hole 33.

Figure 35:
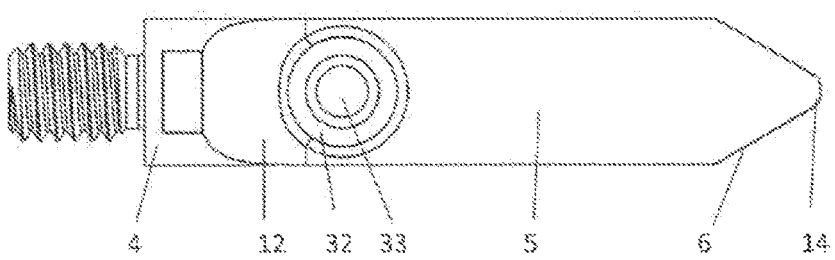
FIG. 35 shows a schematic drawing of an exemplary embodiment of an inventive sonotrode with a support structure.

The thickening or support structure 32 of the sonotrode shown in FIG. 35 is ring shaped with a central round void space 33. The circular void space may be positioned central on the central axis of the blade. Part of the support structure 32 may sit on the flattening area of the sonotrode head 12. The thickening 32 may have maximal thickness between 0.03 and 0.12 mm. Therefore, the thickness of the blade with thickening may be between 0.3 and 0.9 and preferably between 0.4 and 0.7. The outer radius of the ring may be between 3.5 and 5.5 mm, preferably between 4 and 5 mm and the inner radius may be between 2 and 4 mm or further preferred between 2.5 and 3.5 mm.

Figure 36:
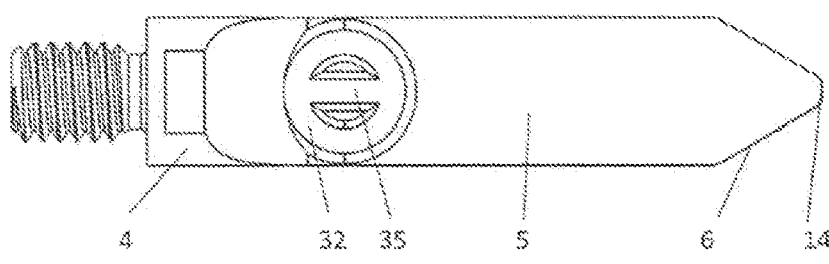
FIG. 36 shows a schematic drawing of an exemplary embodiment of an inventive sonotrode with a support structure.

In FIG. 36 the support structure 32 differs from the one shown in FIG. 35 by a cross beam 35 along the central axis of the blade. The cross beam may have the length of the diameter of the support structure 32. The cross beam reduces the maximal stress during vibration further.

Figure 37:
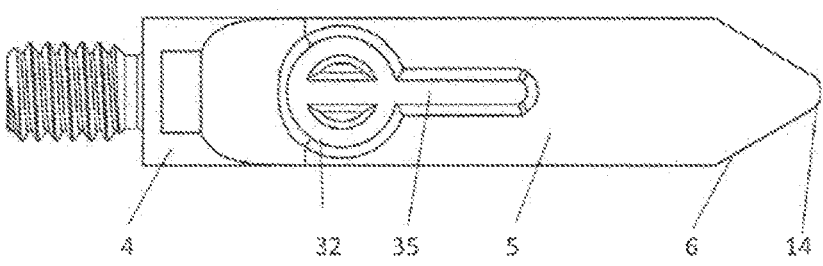
FIG. 37 shows a schematic drawing of an exemplary embodiment of an inventive sonotrode with a support structure.

The support structure 32 as shown in FIG. 37 differs from the one of the sonotrode shown in FIG. 36 by the length of the cross beam, which is longer. The cross beam 35 is lengthen towards the distal end of the blade. This seems to lead to a better distribution of the stress during vibration. The maximal length of the cross beam is 12 mm, further preferred 10 mm. Compared to a ring-shaped support structure without a cross beam the distribution of the bending forces affecting the blade is different. The forces are more widely dispersed. Points of maximal stress are no longer points within the ring but within the cross beam. With the relatively long cross beam the maximal stress can be measured in the area of the cross beam being located distally of the ring. This results in reduced maximal stress and decreases the risk for breaking of the blade.

Figure 38:
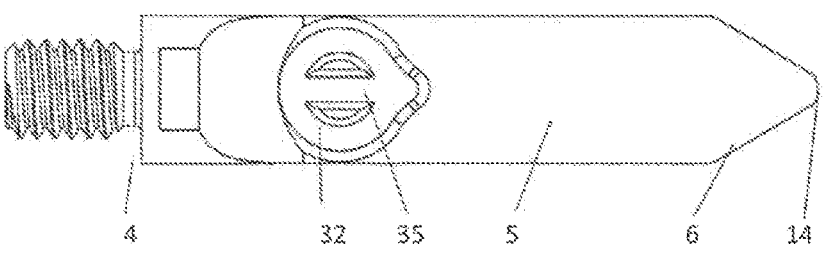
FIG. 38 shows a schematic drawing of an exemplary embodiment of an inventive sonotrode with a support structure.

The support structure 32 as shown in FIG. 38 differs from the one of the sonotrode shown in FIG. 36 by the length of the cross beam, which is slightly longer. This results in a focused stress at the foremost edge.

Figure 39:
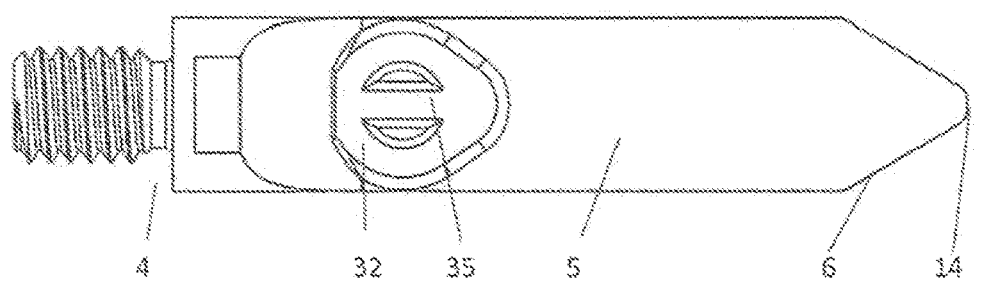
FIG. 39 shows a schematic drawing of an exemplary embodiment of an inventive sonotrode with a support structure.

The support structure 32 of the sonotrode shown in FIG. 39 is ring shaped with a central round void space 33 and an increasing radius at the most distal point. This means the maximal length or the maximal outer radius is half times larger than the minimal outer radius. The support structure 32 is rather egg shaped. It may have a cross beam along the central axis of the blade. The bending forces affecting the blade are widely distributed. Points of maximal stress are the laterally located points of the ring and an area before the support structure. This results in reduced maximal stress and decreases the risk for breaking of the blade. The ring or egg-shaped support structures may have a diameter respectively maximal diameter of 15 to 35% (preferably 18-30% and more preferred 20 to 25%) of the maximal length of the blade. The thickness of the support structure is $\frac{1}{25}$ to $\frac{1}{5}$ (preferably $\frac{1}{20}$ to $\frac{1}{10}$) of the thickness of the blade.

Figure 40:
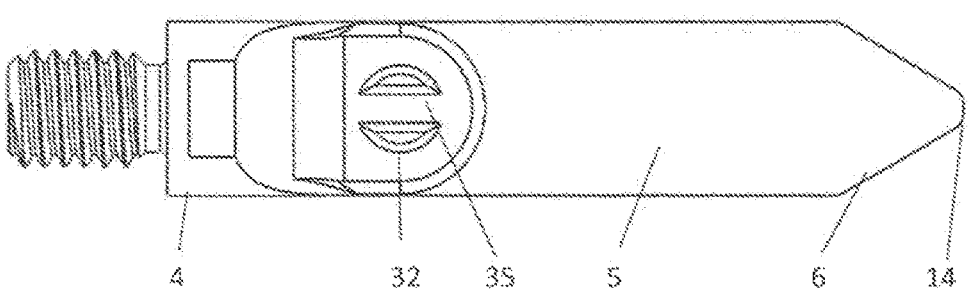
FIG. 40 shows a schematic drawing of an exemplary embodiment of an inventive sonotrode with a support structure.

FIG. 40 shows another variant of a support structure 32, having a central void space 33. It may have a cross beam 35 along the central axis of the blade. The support structure may have a continuous transition to the proximal head of the sonotrode. The radius has been increased so that the outer radius is the same than the width of the sonotrode blade. In addition, the support structure may not be round but rather has the shape of a circular segment (region of a circle) being more than a semicircle. It is preferred that the chord of the circular segment is positioned towards the proximal end (forming a right angle with the central longitudinal axis of the blade). The maximal stress is similar to the one as measured for a sonotrode according to FIG. 38 but the stress distribution seems to be favorable.

Figure 41:
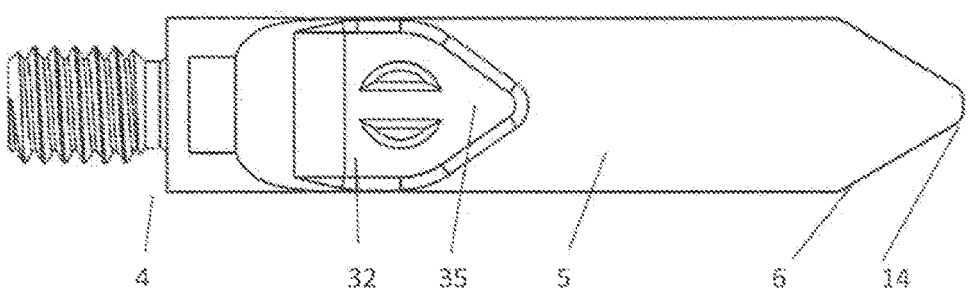
FIG. 41 shows a schematic drawing of an exemplary embodiment of an inventive sonotrode with a support structure.

The support structure 32 as shown in FIG. 41 differs from the one of the sonotrode shown in FIG. 40 by the length of the cross beam 35, which is longer. The cross beam 35 is lengthen towards the distal end of the blade.

Figure 42:
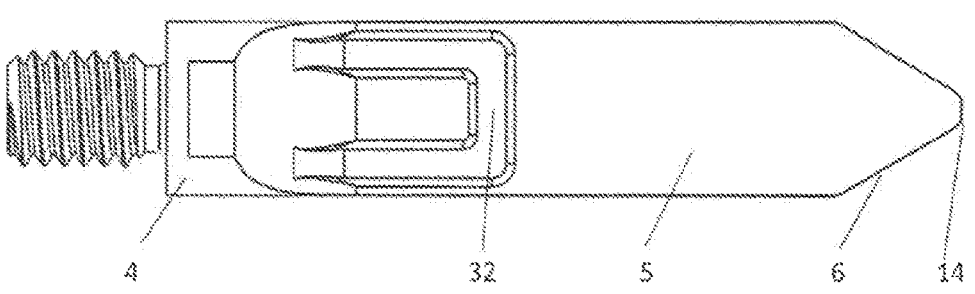
FIG. 42 shows a schematic drawing of an exemplary embodiment of an inventive sonotrode with a support structure.

FIG. 42 shows a sonotrode having a support structure 32 being u-shaped. In other words, the support structure is formed like a rectangular being open at one short side (preferably the proximal side) and having a rectangular central void space. The support structure can consist of two parallel lateral ribs (being parallel to the longitudinal central axis of the blade) with a third rib position in a right angle at the distal end of these ribs. The proximal end may be flattened and ends on the head 4 of the sonotrode.

Figure 43:
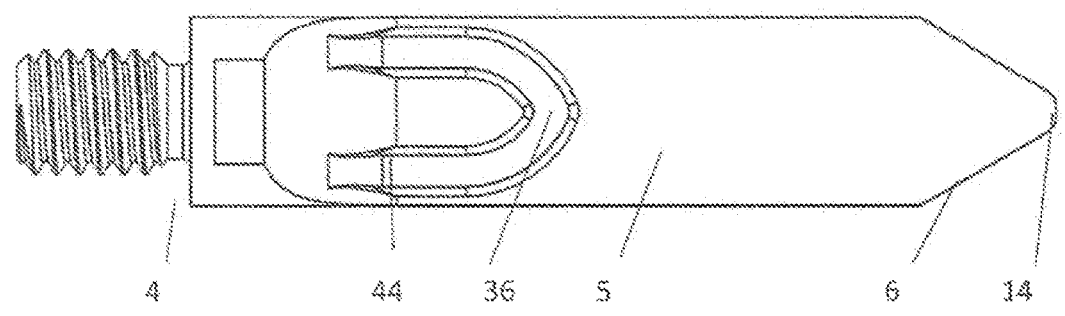
FIG. 43 shows a schematic drawing of an exemplary embodiment of an inventive sonotrode with a support structure.

FIG. 43 shows a sonotrode having a support structure 32 shaped like an arch 36. The arch may be a round arch or semi-circular arch, a parabolic arch or a catenary arch. The arch may be located on two pillars 44. The pillars are located parallel to the longitudinal central axis of the blade 5. The arch points preferably towards the distal end. This means the apex is the most distally located point of the arch, which may be located on the central axis of the blade. The structure 32 may have a length between 3.5 and 10 mm, more preferably between 4.5 and 8 mm and the maximal thickness can be between 0.03 and 0.14 mm. The width is preferably less than the width of the blade. It may be between 3.5 and 5 mm.

Figure 44:
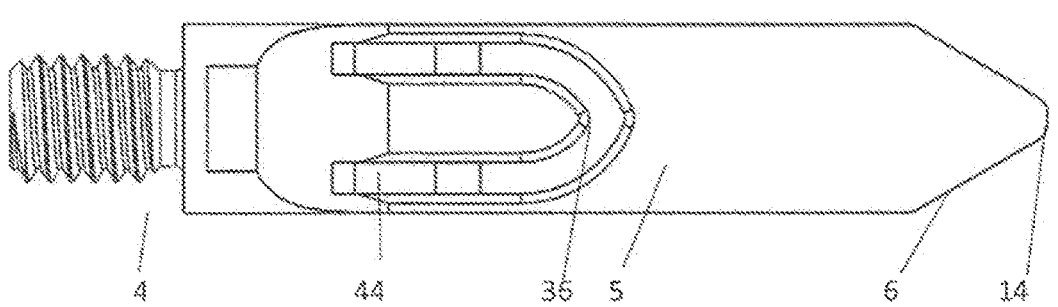
FIG. 44 shows a schematic drawing of an exemplary embodiment of an inventive sonotrode with a support structure.

The support structure 32 as shown in FIG. 44 differs from the one of the sonotrode shown in FIG. 43 by the length of the pillars, which is longer. In addition, the pillar has a proximal part which is thicker than the distal part. The distal part may have a thickness between 0.08 and 0.12 and the proximal part may have a thickness between 0.15 and 0.25. The transition may be stepwise or continuous. The arch 36 is positioned further towards the distal end of the blade. The sonotrode according to FIG. 44 shows the lowest maximal stress during vibration.

Figure 45A:
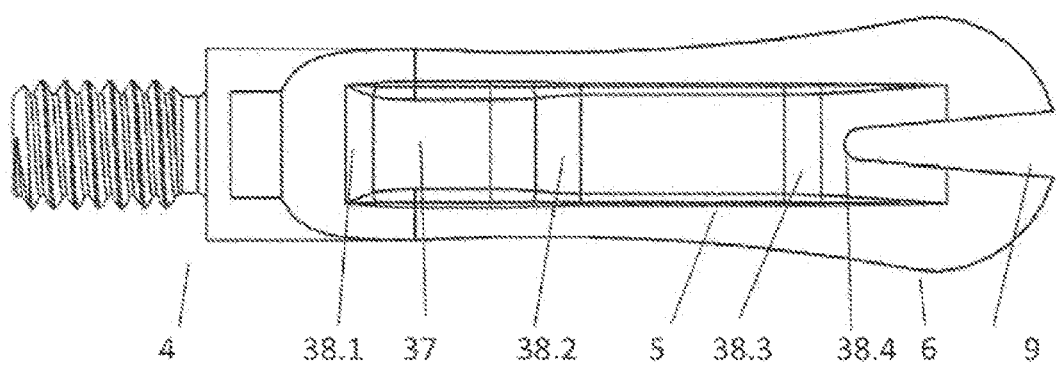
FIGS. 45A-45B are schematic drawings of an exemplary embodiment of an inventive sonotrode with a support structure.
Figure 45B:
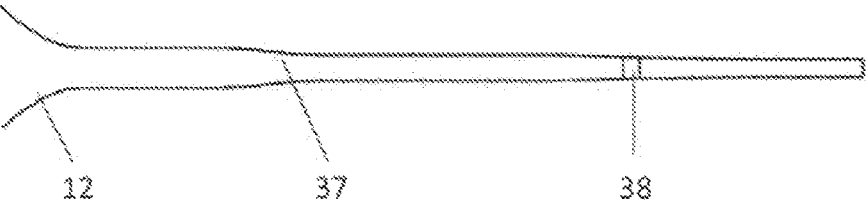

The sonotrodes as shown in FIGS. 45A and 45B are exemplary of the second aspect of the present invention, wherein FIG. 45A illustrates a top view and FIG. 45B shows a section along the central, longitudinal axis. The sonotrode according to FIG. 45A is similar to the sonotrode shown in FIG. 6 and includes a head 4 and a blade 5, the head having at least in its distal end region substantially the same cross section as the proximal end of the blade 5. The distal end of the sonotrode is broadened and has slit 9.

The sonotrode has a wave shaped rib 37 along the central axis of the blade 5. This rib has at least two steps 38 where the thickness decreases. The decrease is favorable a continuous decrease e.g. in form of a linear ramp, gradual slope or curve. The radius of the rounding in area 38.1 is 2 mm, in area 38.2 the radius is 10 mm, in area 38.3 the radius is 30 mm and the step 38.4 has a radius of 100 mm. The thickness of the rib can be between 0.1 and 0.3 mm and in particular between 0.15 and 0.2 mm. The thickness of each step or rectangle can be between 0.05 and 0.20 mm. The width is preferably between 2.5 and 5 mm and preferably between 3 and 4.5 mm. The length of the rib may be between 12 mm and 18 mm. It is preferred that the rib reaches from the head of the sonotrode until the distal area including the slit 9. Therefore, the rib may include a slit. This slit corresponds preferably to the slit of the blade. With other words the slit 9 of the sonotrode reaches also into the rib 37. It is preferred that the rib is attached symmetrically on both sides of the blade as shown in FIG. 45 B.

Figure 46:
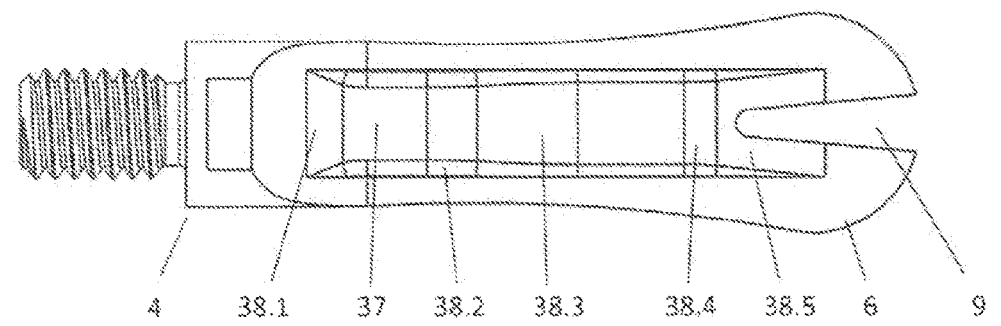
FIG. 46 shows a schematic drawing of an exemplary embodiment of an inventive sonotrode with a support structure.
Figure 47:
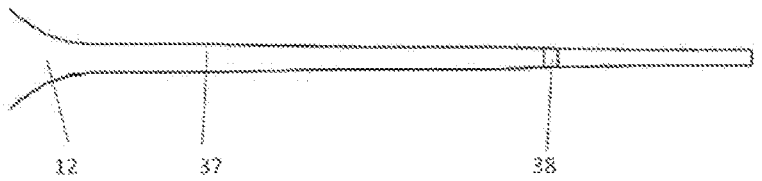
FIG. 47 a longitudinal section of the sonotrode according to FIG. 46.

The sonotrode illustrated in FIGS. 46 and 47 is very similar to the sonotrode according to FIG. 45A, wherein FIG. 46 illustrates a top view and FIG. 47 shows a section along the central, longitudinal axis. The proximal step is very smooth. The step is in form of a ramp with a small slope. Therefore the ramp is rather long. The radius of the rounding in area 38.1 is 3 mm, in area 38.2 the radius is 50 mm, in area 38.3 the radius is 100 mm, in the area 38.4 the radius of the rounding is 30 mm and the step 38.5 has a radius of 100 mm. There may also be more steps. Compared to the sonotrode according to FIG. 6 a very high reduction of maximal stress (about 50%) has been calculated for the sonotrodes according to FIGS. 45 and 46.

Figure 48:
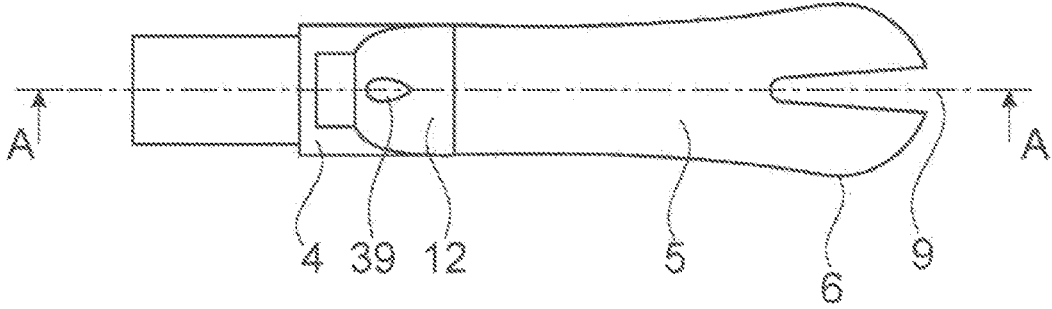
FIG. 48 shows a schematic drawing of an exemplary embodiment of an inventive sonotrode having a cooling system.
Figure 49:
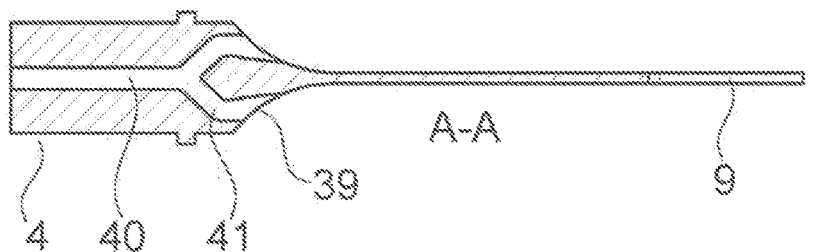
FIG. 49 shows a longitudinal section of the sonotrode according to FIG. 48.
Figure 50:
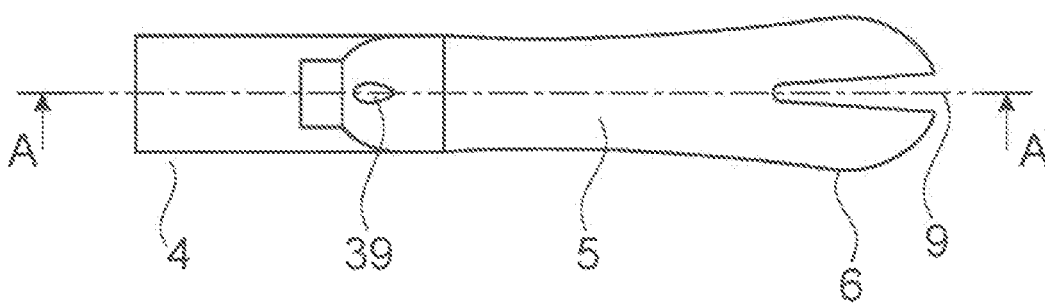
FIG. 50 shows a schematic drawing of an exemplary embodiment of an inventive sonotrode having a cooling system.

FIGS. 48 and 50 show each a schematic drawing of an exemplary embodiment of an inventive sonotrode having a cooling system. Such a cooling system or an analogous cooling system may also be part of a sonotrode having a different design described herein. The cooling system may have at least one exit port at the head 4 of the sonotrode and in particular within the flattening area 12 of the head. It is preferred that an exit port is symmetrically arranged on each side of the sonotrode. The exit port may be located to have a central position, which means the central longitudinal axis of the sonotrode (A-A) runs through the exit port. The feeding channels of the cooling system may vary as shown in FIGS. 49 and 51.

FIG. 49 shows a longitudinal section of the sonotrode according FIG. 48. The system includes a central channel (or main channel) 40 running along the central axis through the housing or hand piece of the sonotrode up to or into the head 4 of the sonotrode. Within the head of the sonotrode the central channel splits into two feeding channels 41 ending with the exit port. The feeding channels may be arranged in a way that the distal end of these channels forms an acute ankle with the longitudinal axis of the sonotrode blade. This ensures that the cooling liquid runs on the blade and further along the blade. Therefore, the longitudinal axis of the first, proximal part of the feeding channels forms with the longitudinal axis of the central channel an angle of 35° to 60°, preferably 40° to 50°. The second, distal part of the feeding channels forms with the longitudinal axis of the central channel an angle of 5° to 15°, preferably 7° to 10°.

Figure 51:
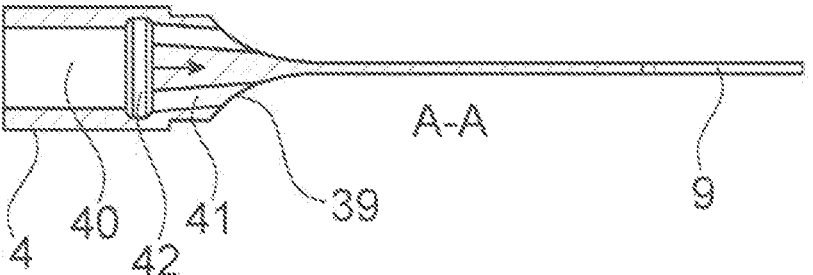
FIG. 51 shows a longitudinal section of the sonotrode according to FIG. 50.

FIG. 51 shows a longitudinal section of the sonotrode according FIG. 50. The system includes a central channel (or main channel) 40 running along the central axis through the housing or hand piece of the sonotrode up to or into the head 4 of the sonotrode. Within the head of the sonotrode the central channel ends in a cavity 42 serving as a reservoir. At the distal end the reservoir has two discharge openings where each a feeding channel 41 starts. The feedings channels end with an exit port 39 within the head 4 of the sonotrode. Between the discharge opening and the exit port is preferably a slope or gradient. Therefore, the longitudinal axis of the feeding channels forms with the longitudinal axis of the central channel an angle of 4° to 15°, preferably 5° to 10°. The sonotrodes including a cooling system as shown in FIGS. 49 and 51 can only be produced using additive manufacturing processes. It is not possible to create the channels as described by drilling.

Figure 12:
FIG. 12 shows results of FEM simulation of a sonotrode according to FIG. 6.
Figure 13:
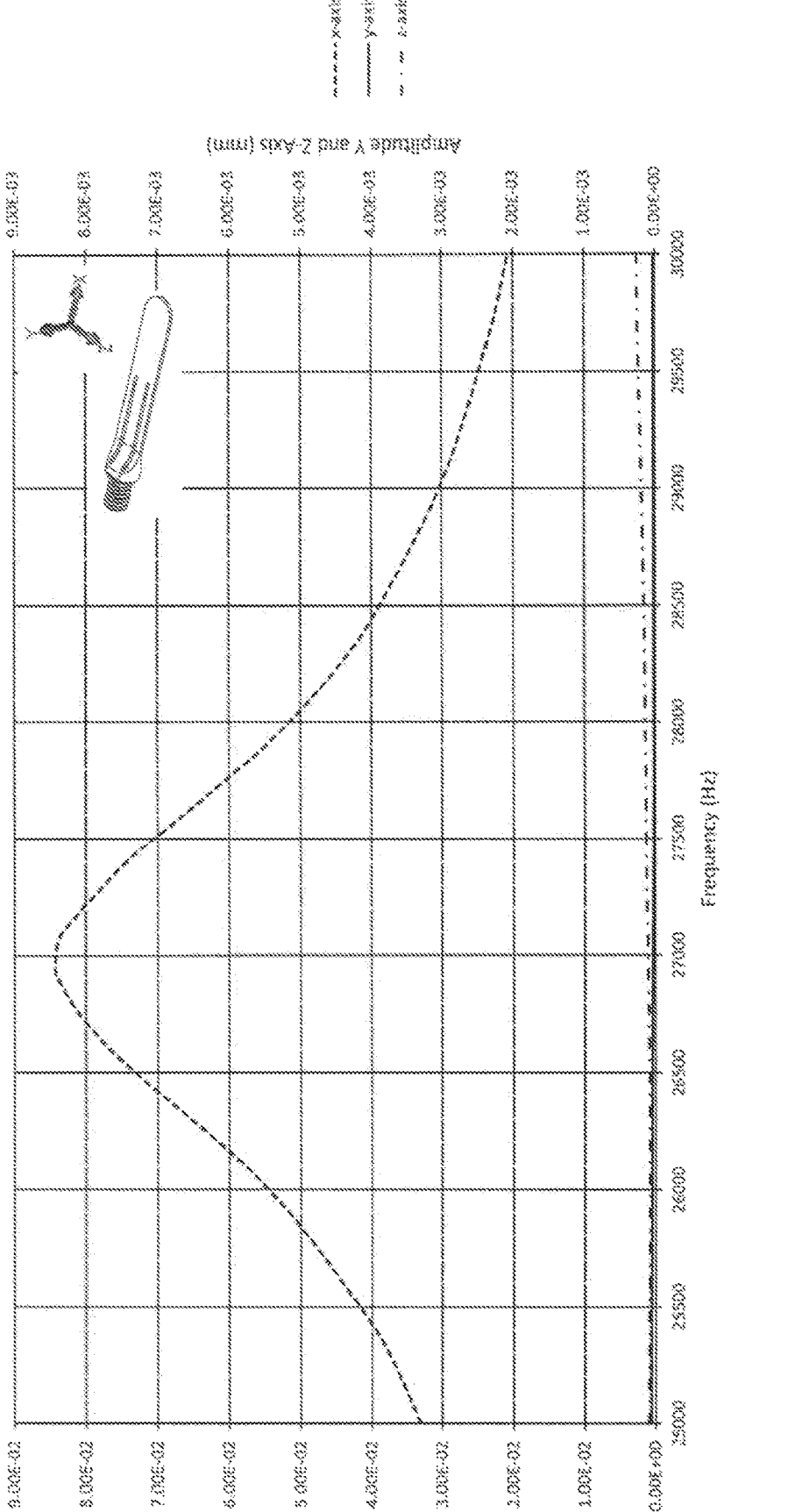
FIG. 13 shows results of FEM simulation of a sonotrode according to FIG. 10.

FEM simulations of some sonotrodes according to the invention were done to determine the resonance frequency and the stress in the material. It gives especially a relationship between the x-y-z amplitudes to have a first understanding of sonotrode movement. The resonance frequency should be around 27 200 Hz in the simulation. Results of a sonotrode according to FIG. 6 are shown in FIG. 12 and in table 1. Results of a sonotrode according to FIG. 10 are shown in FIG. 13 and in table 2. As can be seen in table 1, the sonotrode according to FIG. 6 has a longitudinal resonance frequency of 27.38 kHz. In addition the amplitude in the z-axis is only 10 times smaller. The frequency indirection of the z-axis is negligible. The sonotrode according to FIG. 7 has a longitudinal resonance frequency of 27.32 kHz. The sonotrode according to FIG. 5 has a longitudinal resonance frequency of 27.29 kHz. As can be seen in table 2, the sonotrode according to FIG. 10 has a longitudinal resonance frequency of 27 kHz. In addition, the amplitude in the z-axis and y-axis is negligible. FIG. 12 shows, that the slit together with the broadening at the distal end generates a movement/amplitude in z-direction. FIG. 13 shows the behavior of the sonotrode according to FIG. 10, where only one movement takes place in x and none in z-direction or y-direction.

| Mode | Frequency [Hz] | Type of mode |
|------|----------------|--------------|
| 1 | 26'219 | Bending |
| 2 | 27'378 | Longitudinal |
| 3 | 29'604 | Bending |

Table 1 showing results of FEM simulation of a sonotrode according to FIG. 6

| Mode | Frequency [Hz] | Type of mode |
| --- | --- | --- |
| 1 | 25'060 | Bending |
| 2 | 26'997 | Longitudinal |
| 3 | 27'996 | Bending |

Table 2 showing results of FEM simulation of a sonotrode according to FIG. 10

What is claimed is:

1. A sonotrode for an ultrasonic surgical instrument having a head and a distal end piece, the distal end piece being a blade for cutting bones using mechanical vibration, wherein the blade is flat and extends in a plane defined by the blade, wherein a width of the blade increases toward a distal end of the blade, and wherein the distal end of the blade is arcuate and the blade has exactly one slit, and wherein the slit is at the distal end of the blade and separates the blade into first and second distal blade portions, and wherein a width of the slit increases toward a distal end of the slit and the arcuate distal end of the blade such that a width of each of the first and second distal blade portions decreases toward the arcuate distal end of the blade.

2. The sonotrode according to claim 1, wherein the sonotrode comprises a support structure attached to the proximal end of the blade.

3. The sonotrode according to claim 2, wherein the support structure has the shape of a ring.

4. The sonotrode according to claim 3, wherein the support structure further comprises a cross beam.

5. The sonotrode according to claim 2, wherein the support structure has the shape of an arc.

6. The sonotrode according to claim 5, wherein the apex of the arc points towards the distal end of the blade.

7. The sonotrode according to claim 1, wherein the sonotrode comprises a lateral depression on each side.

8. The sonotrode according to claim 7, wherein the lateral depressions have the same depth and are symmetrically arranged within the blade.

9. The sonotrode according to claim 7, wherein the lateral depressions have each a depth of 0.7 mm-1.2 mm.

10. The sonotrode according to claim 7, wherein the blade of the sonotrode has channels running from the area of the depression to the edge of the blade.

11. The sonotrode according to claim 7, wherein the lateral depression has at least two different levels.

12. The sonotrode according to claim 1, wherein the slit has one of a V-shape, a U-shape or a Y-shape.

13. The sonotrode according to claim 1, wherein the slit runs from a most distal point of the blade distal end towards the head of the sonotrode.

14. The sonotrode according to claim 1, wherein the sonotrode comprises at least one rib.

15. The sonotrode according to claim 14, wherein the sonotrode has at least one lateral rib on each side.

16. The sonotrode according to claim 14, wherein the sonotrode has at least two lateral ribs on each side.

17. The sonotrode according to claim 14, wherein the at least one rib runs along the central axis of the sonotrode.

18. The sonotrode according to claim 14, wherein the at least one rib runs along the head and the distal end piece of the sonotrode.

19. The sonotrode according to claim 14, wherein the at least one rib runs only along the distal end piece of the sonotrode.

20. The sonotrode according to claim 14, wherein the at least one rib has a flattened distal end.

21. The sonotrode according to claim 14, wherein the distal end of the at least one rib lies in the middle third of blade length.

22. The sonotrode according to claim 1, wherein the head has a flattened distal end.

23. The sonotrode according to claim 1, wherein the surface of the sonotrode or the surface of the blade has convex microstructures.

24. The sonotrode according to claim 1, wherein the surface of the sonotrode or the surface of the blade has a roughness average Ra between 5-15 μm.

25. The sonotrode according to claim 1, wherein the sonotrode or at least the blade of the sonotrode is manufactured using an additive manufacturing method.

26. The sonotrode according to claim 1, wherein the blade of the sonotrode has a length of 15 to 40 mm a thickness of 0.3 to 0.6 mm and a width of 3 to 7.5 mm.

27. The sonotrode according to claim 1, having a resonance frequency of 27000 to 27500 Hz.

28. The sonotrode according to claim 1, wherein the blade of the sonotrode has an arcuate distal end portion.

29. An ultrasonic surgical instrument for cutting bones, comprising:
   a hand-piece containing an ultrasonic transducer and
   a sonotrode as defined in claim 1 mechanically coupled to said ultrasonic transducer.

30. A method for manufacturing a sonotrode as defined in claim 1, wherein the sonotrode is manufactured by using an additive manufacturing method.

* * * * *